(12) United States Patent
Breuer et al.

(10) Patent No.: US 8,993,544 B2
(45) Date of Patent: Mar. 31, 2015

(54) CARBAMOYLPHOSPHONATES AS INHIBITORS AND USES THEREOF

(75) Inventors: Eli Breuer, Jerusalem (IL); Reuven Reich, Rehovot (IL); Julia Frant, Modiin (IL); Amnon Hoffman, Jerusalem (IL); Veerendhar Ainelly, Jerusalem (IL)

(73) Assignee: Yissum Research Development Company of the Hebrew University of Jerusalem, Ltd., Jerusalem (IL)

(*) Notice: Subject to any disclaimer, the term of this patent is extended or adjusted under 35 U.S.C. 154(b) by 710 days.

(21) Appl. No.: 13/148,421

(22) PCT Filed: Feb. 9, 2010

(86) PCT No.: PCT/IL2010/000115
§ 371 (c)(1),
(2), (4) Date: Oct. 31, 2011

(87) PCT Pub. No.: WO2010/089752
PCT Pub. Date: Aug. 12, 2010

(65) Prior Publication Data
US 2012/0035140 A1  Feb. 9, 2012

Related U.S. Application Data

(60) Provisional application No. 61/151,041, filed on Feb. 9, 2009.

(51) Int. Cl.
*A61K 31/662* (2006.01)
*C07F 9/44* (2006.01)
*C07F 9/38* (2006.01)
*C07F 9/40* (2006.01)

(52) U.S. Cl.
CPC ............. *A61K 31/662* (2013.01); *C07F 9/3891* (2013.01); *C07F 9/4065* (2013.01)
USPC ............................................ 514/117; 562/15

(58) Field of Classification Search
None
See application file for complete search history.

(56) References Cited

U.S. PATENT DOCUMENTS

2006/0111328 A1   5/2006  Breuer et al.

FOREIGN PATENT DOCUMENTS

| EP | 1074556 A1 | 2/2001 |
| WO | 0126661 A1 | 4/2001 |
| WO | 2004089962 A2 | 10/2004 |

OTHER PUBLICATIONS

Hoffman, A. et al., "Carbamoylphosphonate Matrix Metalloproteinase Inhibitors 6: cis-2-Aminocyclohexylcarbamoylphosphonic Acid, A Novel Orally Active Antimetastatic Matrix Metalloproteinase-2 Selective InhibitorsSynthesis and Pharmacodynamic and Pharmacokinetic Analysis", Journal of Medicinal Chemistry, vol. 51, pp. 1406-1414 (2008).
Reiter, L. A. et al., "Potent, selective pyrimidinetrione-based inhibitors of MMP-13", Bioorganic & Medicinal Chemistry Letters, vol. 16, pp. 5822-5826, (2006).
Rossello, A. et al., "New N-arylsulfonyl-N-alkoxyaminoacetohydroxamic acids as selective inhibitors of gelatinase A (MMP-2)", Bioorganic & Medicinal Chemistry Letters, vol. 12, pp. 2441-2450, (2004).
Shyh-Ming, Yang et al., "beta-N-Biaryl ether sulfonamide hydroxamates as potent gelatinase inhibitors: Part 1. Design, synthesis, and lead identification", Bioorganic & Medicinal Chemistry Letters, vol. 18, pp. 1135-1139, (2008).
Wada, C. K. et al., "Phenoxyphenyl Sulfone N-Formylhydroxylamines (Retrohydroxamates) as Potent, Selective, Orally Bioavailable Matrix Metalloproteinase Inhibitors", Journal of Medicinal Chemistry, vol. 45, pp. 219-232 (2002).

*Primary Examiner* — Bong-Sook Baek
(74) *Attorney, Agent, or Firm* — Browdy and Neimark, PLLC

(57) ABSTRACT

The present invention relates to novel metalloproteinase inhibitors having an aryloxybenzenesulfonamide moiety and a carbamoylphosphonic acid moiety, to pharmaceutical compositions comprising them, and to their uses in the prevention and/or treatment of disease or disorder associated with MMP.

32 Claims, 5 Drawing Sheets

CARBAMOYLPHOSPHONATES AS INHIBITORS AND USES THEREOF

FIELD OF THE INVENTION

The present invention is generally in the field of inhibitors for metalloproteinase.

BACKGROUND OF THE INVENTION

Matrix Metalloproteinase (MMP) and A Disintegrin And Metalloproteinase (ADAM) are a family of structurally-related zinc-containing enzymes. MMPs are secreted as inactive proenzymes, which become active enzymes following proteolytic cleavage of the peptide amino-terminal domain or conformational modification.

MMPs and ADAMs are involved in the breakdown of extracellular matrix in normal physiological processes, such as embryonic development, reproduction, and tissue remodeling. Defects in the regulation of these enzymes can result in pathological destruction of the tissue. A wide range of diseases or disorders may result from the loss of regulation control of matrix metalloproteinases, such as multiple sclerosis, restenosis, aortic aneurism, heart failure, periodontal disease, corneal ulceration, burns, decubital ulcers, chromic ulcers or wounds, cancer metastasis, tumor angiogenesis, arthritis, psoriasis and autoimmune and inflammatory diseases arising from tissue invasion by leukocytes.

Previous studies have suggested that inhibition of MMPs and ADAMs may be applicable in the treatment of diseases.

WO 01/26661 [1] concerns alpha-oxophosphonates or alpha-thioxophosphonates as effective compounds in inhibiting zinc containing proteinases, particularly matrix metalloproteinases, to control the invasiveness of cancer cells.

WO 04/089962 [2] concerns a specific group of compounds having carbamoyl- or thiocarbamoylphosphonate functionalities and are considered to be improved MMP-2 inhibitors.

Rossello A. et al., [3] report on new N-arylsulfonyl-N-alkoxyamino acetohydroxamic acid as selective inhibitors of MMP-2.

Wada C. K. et al., [4] report on a group of compounds having a phenoxyphenyl functionality which are selective for inhibition of MMP-2 and MMP-9 over MMP-1.

Shyh-Ming Yang et al., [5] report on a series of β-N-biaryl ether sulfonamide hydroxamates as of MMP-2 and MMP-9 inhibitors.

Reiter L. A. et al., [6] report on a series of selective pyrimidinetrione-based inhibitors of MMP-13.

Hoffman A. et al., [7] report on carbamoylphosphonate derivatives for use as MMP inhibitors.

REFERENCES

[1] WO 01/26661
[2] WO 04/089962
[3] Rossello A. et al., Bioorganic & Medicinal Chemistry (2004) 12, 2441-2450
[4] Wada C. K. et al., J. Med. Chem. (2002) 45, 219-232
[5] Shyh-Ming Yang et al., Bioorganic & Medicinal Chemistry Letters (2008) 18, 1135-1139.
[6] Reiter L. A. et al., Bioorganic & Medicinal Chemistry Letters (2006) 16, 5822-5826.
[7] Hoffman, A. et al., J. Med. Chem. (2008) 51, 1406-1414.

SUMMARY OF THE INVENTION

The present invention concerns matrix metalloproteinase (MMP) inhibitors of increased affinity based on carbamoylphosphonic acids. As used herein, the term "MMP" refers to a matrix metalloproteinase. The MMPs belong to the MMP superfamily as represented by at least 26 extracellular matrix-degrading metal peptidases active during tissue development and differentiation, cellular infiltration, wound healing, and as moderators of the immune response.

In one aspect of the present invention, there is provided a compound having an aryloxybenzenesulfonamide moiety and a carbamoylphosphonic acid (or a derivative thereof) moiety.

In some embodiments, the aryloxybenzenesulfonamide moiety is associated to the carbamoylphosphonic acid moiety via a bond or a group. In some embodiments, the association between the moieties is via a covalent bond, via an ionic bond or via a linker group comprising optionally at least one atom selected from C, N and O.

In further embodiments, said aryloxybenzenesulfonamide and carbamoylphosphonic acid moieties are bonded to each other via a linker group selected amongst aliphatic moieties (a moiety comprising at least one —CH— or —CH$_2$—groups).

As a person versed in the art would appreciate, the aryloxybenzenesulfonamide moiety, as referred to herein, is the moiety having an aryloxy group (aryl bonded to at least one O atom) bonded to a benzenesulfonamide moiety. The aryl of the aryloxy group may be selected from aromatic ring systems, which may or may not be fused. In some embodiments, the aryloxy is selected from phenoxy, naphthoxy and derivatives thereof.

In some embodiments of the invention, the aryloxybenzenesulfonamide moiety is a phenoxybenzenesulfonamide (or a derivative thereof) having the structure:

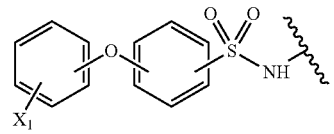

wherein the two aromatic rings, demonstrated for the purpose of brevity as two phenyl rings, are bonded to each other through the linking oxygen atom. The phenyl ring shown to be connected to a variant $X_1$ is referred to as a phenoxy and the phenyl ring bonded to the sulfonamide (—SO$_2$NH—) group is referred to as a benzenesulfonamide.

The substitution of the sulfonamide on the phenyl ring may be at any position relative to the aryloxy, e.g., phenoxy group. In some embodiments, the sulfonamide is substituted ortho, meta or para to the bond with the aryloxy, e.g., phenoxy group.

In other embodiments, the substituent $X_1$ is one or more substituents on any of the two rings constituting the aryloxybenzene, e.g., phenoxybenzene moiety. In some embodiments, the substitution of the sulfonamide may be ortho, meta or para to any one substituent which may be present on the ring.

In further embodiments, the substituent $X_1$ is at any position on any of two rings (or ring systems in e.g., naphthoxy). In other words, the aryloxybenzene, e.g., phenoxybenzene moiety may comprise two or more X substituents, independently at any one or more positions of any of the rings, wherein each further substituent is designated $X_2, X_3, X_4$, etc. Such multi-substituted aryloxybenzene, e.g., phenoxybenzene moiety may have the following general structure:

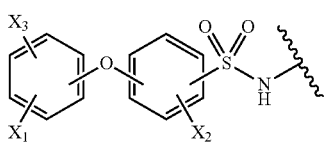

As used herein, the carbamoylphosphonic acid moiety is the moiety:

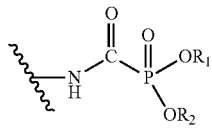

wherein each of $R_1$ and $R_2$ is as defined herein.

In further embodiments, the compound of the invention is of the general formula (I):

G-L-Q  (I)

wherein
G is an aryloxybenzenesulfonamide moiety, as defined;
L is a linker moiety; and
Q is a carbamoylphosphonic acid moiety or derivative thereof (i.e., wherein one or both of $R_1$ and $R_2$ are different from —H).

In the compound of formula (I), G is bonded to L via a covalent bond and L is bonded to Q via a covalent bond.

In some embodiments, the linker moiety L is an atom or a group of atoms bonding said G group and Q group via a covalent bond, which may or may not be hydrolyzable.

In some embodiments, the linker moiety L is a carbon chain of at least two carbon atoms. In further embodiments, said carbon chain is a $C_2$-$C_{10}$-alkylene, the alkylene being optionally substituted by one or more groups, atoms or heteroatoms selected from N, O and S. In other embodiments, said $C_2$-$C_{10}$-alkylene is interrupted by at least one heteroatom selected from N, O and S.

In other embodiments, said $C_2$-$C_{10}$-alkylene is substituted by one or more groups A. The substituting group A is selected, in a non-limiting manner, from —H; halo (Br, Cl, I or F); —$C_1$-$C_6$-alkyl; —$C_2$-$C_6$-alkenyl; —$C_2$-$C_6$-alkynyl; —$C_3$-$C_6$-cycloalkyl; —$CF_3$; —$C_6$-$C_{10}$-aryl; —OH; —O—$C_1$-$C_6$-alkyl; —$NO_2$; —$N_3$, and —NR'R", wherein each of said R' and R", independently of each other, is selected from —H, —$C_1$-$C_6$-alkyl and —C(O)O-t-Bu; R' and R" together with the N atom to which they are bonded may form a heterocyclic ring of between 3 and 6 carbon atoms, optionally further comprising at least one additional heteroatom selected from N, O and S.

In some embodiments, in the compound of formula (I), G is a phenoxybenzenesulfonamide moiety, being optionally substituted.

In further embodiments, the compound of formula (I) is a compound of formula (II):

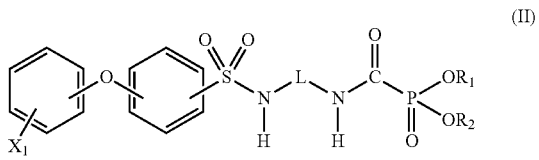

wherein
L is a linker moiety, as defined hereinabove, being optionally substituted with A, as defined above;

$X_1$ is at least one substituent selected from —H; halo (Br, Cl, I or F); —$C_1$-$C_6$-alkyl; —$C_2$-$C_6$-alkenyl; —$C_2$-$C_6$-alkynyl; —$C_3$-$C_6$-carbocyclic rings; —$C_6$-$C_{10}$-aryl; —$CF_3$; —OH; —O—$C_1$-$C_6$-alkyl; —$NO_2$; —$NHC(O)R_3$; and —NR'R", wherein each of said R' and R", independently of each other, is selected from —H and —$C_1$-$C_6$-alkyl;

each of $R_1$ and $R_2$, independently of each other, is selected from —H, —$C_1$-$C_6$-alkyl, —$CR_4R_5$—O—(O)C—$C_1$-$C_6$-alkyl and a cation, said cation being selected, in some embodiments, from cations of at least one pharmaceutically acceptable base;

R' and R" together with the N atom to which they are bonded may form a heterocyclic ring of between 3 and 6 carbon atoms, which optionally further comprise at least one additional heteroatom selected from N, O and S;

$R_3$ is selected from —$C_1$-$C_6$-alkyl; —$C_2$-$C_6$-alkenyl; —$C_2$-$C_6$-alkynyl; —$C_3$-$C_6$-carbocyclic rings; —O—$C_1$-$C_6$-alkyl; —$CF_3$; and —$C_6$-$C_{10}$-aryl; and each of $R_4$ and $R_5$, independently of each other, is selected from —H and $C_1$-$C_6$-alkylene.

In some embodiments of a compound of formula (II), the linker moiety L is a —$C_2$-$C_{10}$-alkylene, said compound is a compound of formula (III):

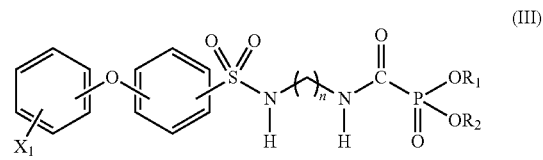

wherein
$X_1$, $R_1$ and $R_2$ are as defined above; and
n is an integer from 2 to 10.

In some embodiments, n is 2, 3, 4, 5, 6, 7, 8, 9 or 10. In further embodiments, n is between 2 and 4, between 4 and 7, between 8 and 10, or between 2 and 8. In some embodiments, n is an integer between 2 and 8, and said $C_2$-$C_{10}$-alkylene is $C_2$-$C_8$-alkylene selected, in some embodiments, from ethylene (—$CH_2CH_2$—), propylene (—$CH_2CH_2CH_2$), butylenes (—$CH_2CH_2CH_2CH_2$—), pentylene (—$CH_2CH_2CH_2CH_2CH_2$—), hexylene (—$CH_2CH_2$—$CH_2CH_2$—$CH_2CH_2$—), heptylene (—$CH_2CH_2CH_2CH_2CH_2CH_2$—) and octylene (—$CH_2$—$CH_2CH_2CH_2CH_2CH_2CH_2$—).

In some embodiments, the $C_2$-$C_{10}$-alkylene is substituted by at least one substituent A, as defined above, on any one or more of the carbon atoms of the alkylene moiety. In other embodiments, said $C_2$-$C_8$-alkylene is substituted by at least one A.

In other embodiments, the compound of formula (III) is a compound of formula (IV):

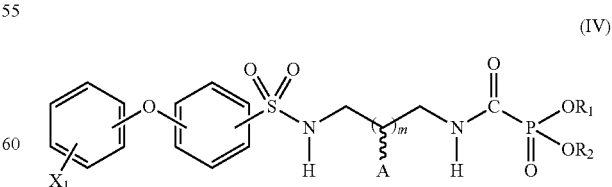

wherein the wavy bond to A indicates a specific isomer R or S or any mixture thereof, e.g. racemic mixture, and wherein each of $X_1$, $R_1$, $R_2$ and A is as defined above and m is from 0 to 8.

In some embodiments, in the compound of formula (IV) the linker moiety, linking G and Q is substituted by one A. In other embodiments, the linker is substituted by at least two A groups, only one of which being different from —H. In further embodiments, the linker is substituted by at least two A groups, at least one of which being different from —H.

As recited above, A is selected, in a non-limiting manner, from —H; halo (Br, Cl, I or F); —$C_2$-$C_6$-alkenyl; —$C_2$-$C_6$-alkynyl; —$C_3$-$C_6$-cycloalkyl; —$CF_3$; —$C_6$-$C_{10}$-aryl; —OH; —O—$C_1$-$C_6$-alkyl; —$NO_2$; —$N_3$; and —NR'R", wherein each of said R' and R", independently of each other, is selected from —H, —$C_1$-$C_6$-alkyl and —C(O)—O-t-Bu; R' and R" together with the N atom to which they are bonded may form a heterocyclic ring of between 3 and 6 carbon atoms, optionally further comprising at least one additional heteroatom selected from N, O and S.

Where the linker moiety is substituted by two or more A groups, each A may be selected to be the same or different. For example, where the alkylene linker is substituted by two A residues, one A may be —$NH_2$ and the other may be —H. According to another example, where the alkylene linker is substituted by two or more A residues, only one of which may be different from —H and the remaining may each be —H.

In another example, in the formula (IV) m is 3 and thus the linker is of the structure G-$CH_2$—CH(A)-CH(A)-CH(A)-$CH_2$-Q (wherein G and Q are the moieties defined above). In such a structure of the linker, at least one of the substituents A is different from —H and the remaining As are each —H; thus, at least three such mono-A structures are possible: G-$CH_2$—CH(A)-$CH_2$—$CH_2$—$CH_2$-Q, G-$CH_2$—$CH_2$—CH(A)-$CH_2$—$CH_2$-Q and G-$CH_2$—$CH_2$—$CH_2$—CH(A)-$CH_2$-Q, wherein in each of the three exemplified structures, A is different from —H. Similarly, where the linker is substituted by a plurality of A groups, such combination may also be possible.

In some embodiments, in the compound of any one of formulae (I)-(IV) the phenoxybenzene moiety is at the para position to the sulfonamide. A compound of formula (IV), for example, is thus a compound of formula (V):

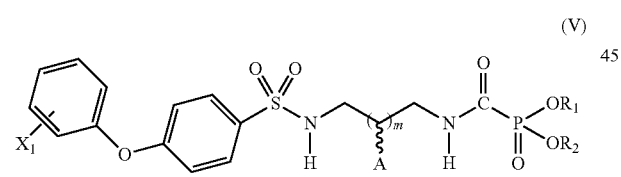

(V)

wherein the wavy bond to A indicates a specific isomer R or S or any mixture thereof, e.g. racemic mixture, and wherein each of $X_1$, A, $R_1$, $R_2$ and m are as defined herein.

In some embodiments, in the compound of formula (V) each one of $X_1$, $R_1$ and $R_2$ is —H or $C_1$-$C_6$-alkyl, and A is selected from —H and —NR'R", wherein R' and R" are each as defined above.

In further embodiments, in the compound of formula (V) each of A, $X_1$, $R_1$ and $R_2$ is —H and wherein:
  m=0, the compound herein designated Compound 1;
  m=1, the compound herein designated Compound 2;
  m=2, the compound herein designated Compound 3;
  m=3, the compound herein designated Compound 4;
  m=4, the compound herein designated Compound 5;
  m=5, the compound herein designated Compound 6; and
  m=6, the compound herein designated Compound 7.

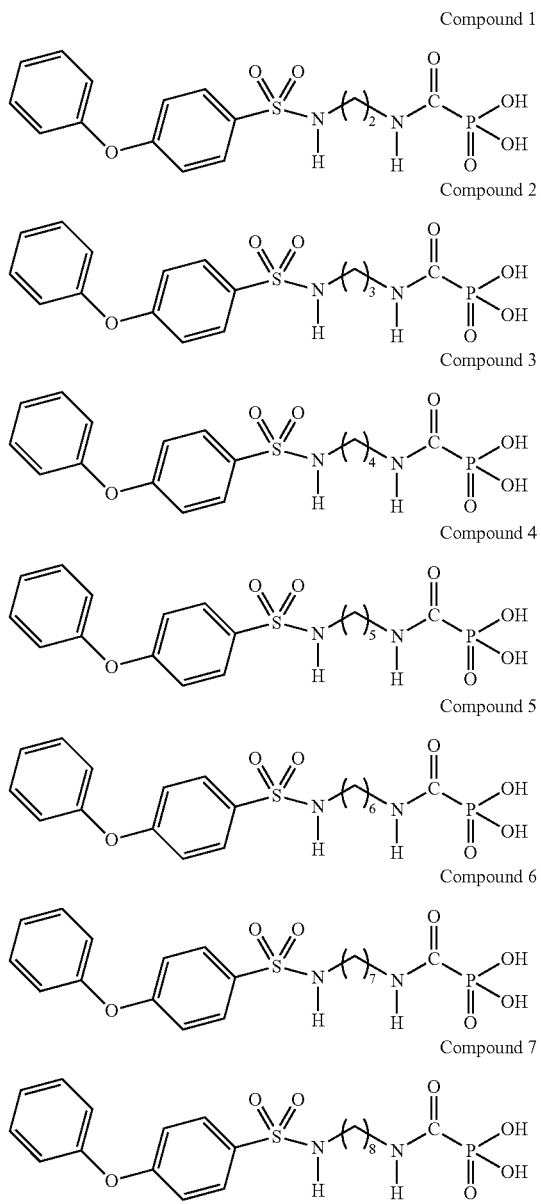

In further embodiments, in the compound of formula (V) each of $X_1$, $R_1$ and $R_2$ is —H and A is different from —H. In some embodiments, m is 1 and A is —NHR", wherein R" is as defined above. In further embodiments, R" is —H and the compound is herein designated Compound 8, wherein the wavy bond to the amine group indicates a mixture, e.g., racemic mixture, of R and S enantiomers.

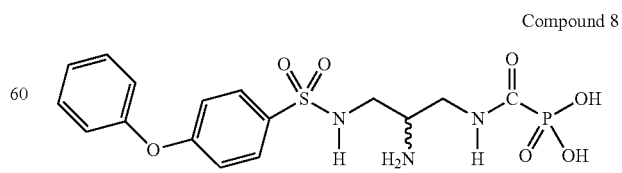

Compound 8

In further embodiments, in the compound of formula (V) each of A and $X_1$, are —H and each of $R_1$ and $R_2$, independently of each other, is $C_1$-$C_6$-alkyl. In some embodiments, each of $R_1$ and $R_2$, independently of each other is selected from $C_1$-$C_3$-alkyl and —$CR_4R_5$—O(O)C—$C_1$-$C_6$-alkyl, wherein each of $R_4$ and $R_5$ are as defined above. Exemplary compounds of formula (V) are:

m=0, each of $R_1$ and $R_2$ is iso-propyl, the compound herein designated Compound 1A;

m=1, each of $R_1$ and $R_2$ is iso-propyl, the compound herein designated Compound 2A;

m=2, each of $R_1$ and $R_2$ is ethyl, the compound herein designated Compound 3A;

m=3, each of $R_1$ and $R_2$ is ethyl, the compound herein designated Compound 4A;

m=4, each of $R_1$ and $R_2$ is ethyl, the compound herein designated Compound 5A.

Compound 1A

Compound 2A

Compound 3A

Compound 4A

Compound 5A

In further embodiments, in the compound of formula (V) $X_1$ is —H, each of $R_1$ and $R_2$ is $C_1$-$C_6$-alkyl or —$CR_4R_5$—O(O)C—$C_1$-$C_6$-alkyl and A is different from —H, wherein each of $R_4$ and $R_5$ are as defined above. In some embodiments, m is 1 and A is selected from —$N_3$ and —NR'R", wherein R' is —H and R" is selected from —$C_1$-$C_6$-alkyl and —C(O)O-t-Bu.

In some embodiments, in a compound of formula (V), $X_1$ is —H, m is 1, each of $R_1$ and $R_2$ is ethyl, and A is —NHC(O)O-t-Bu, the compound is herein designated Compound 8A.

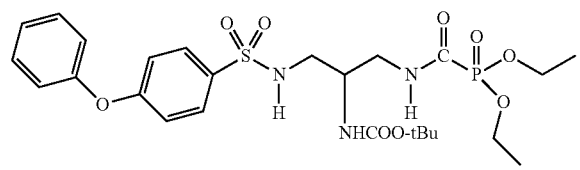

Compound 8A

In some embodiments, in a compound of formula (V), $X_1$ is —H, m is 1, each of $R_1$ and $R_2$ is ethyl, and A is —$N_3$, the compound is herein designated Compound 9.

Compound 9

In other embodiments, in a compound according to formula (I), the linker moiety, L, is a $C_2$-$C_{10}$-alkylene interrupted by at least one heteroatom selected from N, O and S.

As used herein, the expression "$C_2$-$C_{10}$ alkylene interrupted by at least one heteroatom selected from N and O" refers to an alkylene ether generally having the structure "—$C_2$-$C_9$-alkylene-O—$C_2$-$C_9$-alkylene-" (where the heteroatom is oxygen) or alkylene amine (secondary, tertiary or quaternary) generally having the structure "—$C_2$-$C_9$-alkylene-$NR_6$—$C_2$—$C_9$-alkylene-" (where the heteroatom is nitrogen), wherein $R_4$ defines further substitution on the N atom (one or two substitutions). The position of the heteroatom may be between any two carbons of the alkylene ($CH_2$) atoms. The total number of carbon atoms in the linker L at most 10 carbons (i.e., does not exceed 10 carbons).

Thus, a compound of formula (I) wherein the linker moiety, L, is a $C_2$-$C_{10}$-alkylene interrupted by at least one heteroatom selected from N, O and S, is a compound of formulae (VI):

(VI)

wherein each of $X_1$, $R_1$ and $R_2$ are as defined above, and wherein Z is O or S or —$NR_6$; $R_6$ is selected from —H; —$C_1$-$C_6$-alkyl; —$C_2$-$C_6$-alkenyl; —$C_2$-$C_6$-alkynyl; —$C_3$-$C_6$-cycloalkyl; —$CF_3$; and —$C_6$-$C_{10}$-aryl; and each of k and y, independently of each other is an integer between 1 and 9. In some embodiments, integer k and y, independently of each other, is between 2 and 9. In further embodiments, the integer k is different form the integer y. In further embodiments, each of k and y is 2.

In some embodiments, the total number of carbon atoms in the linker moiety is at most 10 (i.e., does not exceed 10 carbons).

In some embodiments, each of k and y is 2 and Z is —NR$_6$, wherein R$_6$ is selected from —H and —C$_1$-C$_6$-alkyl. In some embodiments, R$_6$ is —CH$_3$.

In some embodiments, Z is oxygen and in other embodiments Z is —NH—. In other embodiments, the compound is a compound of formula (VII):

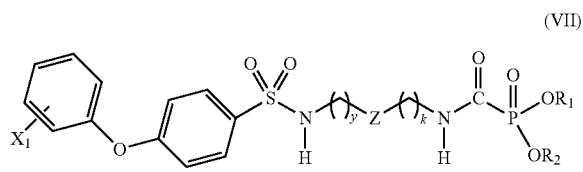

(VII)

wherein each of X$_1$, Z, k, y, R$_1$ and R$_2$ are as defined above.

In some embodiments, in a compound of formula (VII), each of X$_1$, R$_1$ and R$_2$ is —H, Z is —NH, each of k and y is 2, the compound is hereby designated Compound 10.

Compound 10

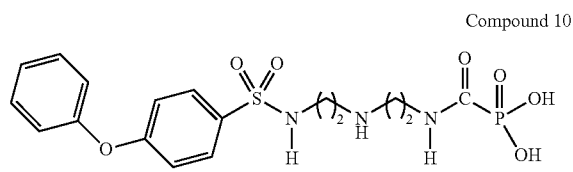

It is to be understood that the compounds provided herein may contain one or more chiral centers. Such chiral centers may be of either the (R) or (S) configuration, or may be a mixture thereof. Thus, the compounds of any one of formulae (I) to (VII) having at least one substituent on the linker moiety may have one or more chiral centers and thus may be enantiomerically pure, or be stereoisomeric or diastereomeric mixtures.

Thus, the invention provides chiral compounds such as those having in the linker moiety at least one A group; in some embodiments having one or two A groups. Such compounds are Compound 8, Compound 8A and Compound 9, each provided herein in their respective (R) or (S) forms, and each as a racemic mixture of the two respective enantiomers.

The enantiomers of Compound 8 are herein designated Compound 8R, in its (R) form and Compound 8S, in its (S) form, and any mixture thereof, e.g., racemic or as enantiomerically enriched mixtures.

It is also to be understood that the chiral centers of the compounds provided herein may undergo epimerization in vivo. As such, one of skill in the art will recognize that administration of a compound in its (R) form is equivalent, for compounds that undergo epimerization in vivo, to administration of the compound in its (S) form.

The term "alkylene" as used herein refers to an alkanediyl functional group having two free-valence carbon atoms, namely an alkyl group substituted at both ends. The alkanediyl may be a linear or a branched. The expression "C$_2$-C$_{10}$ alkylene" refers to such an alkyl group having between 2 and 10 carbon atoms. Similarly, "C$_1$-C$_6$ alkylene" is an alkanediyl group having between 1 and 6 carbon atoms. Non-limiting examples of such alkylenes are ethylene (—CH$_2$CH$_2$—), propylene (—CH$_2$CH$_2$CH$_2$—), isopropylene (—CH(CH$_3$)CH$_2$— or —CH$_2$CH(CH$_3$)—), isobutylene (such as —CH$_2$CH(CH$_3$)CH$_2$— or —CH(CH$_3$)CH$_2$CH$_2$—), butylene (—CH$_2$CH$_2$CH$_2$CH$_2$—), pentylene (—CH$_2$CH$_2$CH$_2$CH$_2$CH$_2$—), hexylene (—CH$_2$CH$_2$CH$_2$CH$_2$CH$_2$CH$_2$—), heptylene (—CH$_2$CH$_2$CH$_2$CH$_2$CH$_2$CH$_2$CH$_2$—), octylene (—CH$_2$CH$_2$CH$_2$CH$_2$CH$_2$CH$_2$CH$_2$CH$_2$—) and others as known in the art.

The term "C$_3$-C$_6$-cycloalkylene" similarly refers to a cyclic alkanediyl being substituted at one carbon atoms or at two different atoms.

Additionally, as may be known to a person skilled in the art, the term "C$_1$-C$_6$ alkyl" refers to an aliphatic chain of between 1 and 6 carbon atoms, being connected to the main structure at one position only. Non-limiting examples of alkyl groups are methyl, ethyl, propyl, isopropyl, isobutyl, n-butyl, sec-butyl, tent-butyl, iso-hexyl, pentyl, hexyl, and others. The term "C$_2$-C$_6$ alkenyl" refers to a carbon chain having between 2 and 6 carbon atoms and at least one C-C double bond. The term "C$_2$-C$_6$ alkynyl" refers to a carbon chain having between 2 and 6 carbon atoms and at least one C—C triple bond.

As used herein, the term "—C$_6$-C$_{10}$-aryl" refers to an aromatic ring moiety having between 6 and 10 carbon atoms. The ring moiety may be a single aromatic ring moiety, e.g., a phenyl, or a fused aromatic ring system such as naphthyl.

The term "—O—C$_1$-C$_6$-alkyl" refers to an oxygen-containing group bonded to C$_1$-C$_6$-alkyl, being as defined above.

The —NR'R" group refers to an amine group, wherein each of said R' and R" independently of each other is selected as defined to afford a primary, secondary or tertiary amine. The two R' and R" groups may together with the N atom to which they are bonded form a heterocyclic ring comprising between 3 and 6 carbon atoms, and optionally one or more additional heteroatom selected from N, O and S.

As used herein, the term "—CR$_4$R$_5$—O—(O)C—C$_1$-C$_6$-alkyl" refers to an alkyl group, as defined above, connected to an acyloxy moiety, generally of the structure —CR$_4$R$_5$—O—(O)C—, wherein R$_4$ and R$_5$ are as defined above.

The compounds of the invention may contain at least one basic atom or substituent, and thus are capable of forming a wide variety of different salts with various inorganic and organic acids. Although such salts must be pharmaceutically acceptable for administration to animals (human and non-human), it is often desirable in practice to initially isolate the base compounds from the reaction mixture as other non-acceptable salts, such as perchlorates, picolinates, picrates, or the like, and then convert them to the free base compound by treatment with an alkaline reagent, as known to a person skilled in the art. Subsequently, the free base forms may be converted to the pharmaceutically acceptable acid addition salts.

The acid addition salts of the compounds of this invention are readily prepared by treating the compounds with equivalent amounts of a chosen mineral or organic acid in an aqueous solvent or in a suitable organic solvent, such as methanol or ethanol. The desired solid salt may then be readily obtained by, e.g., evaporation of the solvent.

The pharmaceutically acceptable acid forms of the compounds of the invention, are obtained from non-toxic acid addition salts, i.e., salts containing pharmaceutically acceptable anions, such as the hydrochloride, hydrobromide, hydroiodide, nitrate, sulfate or bisulfate, phosphate or acid phosphate, acetate, lactate, citrate or acid citrate, tartrate or bi-tartrate, succinate, maleate, fumarate, gluconate, saccharate, benzoate, methanesulfonate, ethanesulfonate, benzenesulfonate, and p-toluenesulfonate.

Certain compounds of the present invention have at least one acidic group and are thus capable of forming base salts with various pharmaceutically acceptable cations. Examples of such salts include the alkali metal or alkaline-earth metal salts and, particularly, the sodium and potassium salts.

As stated above, in certain embodiments of the invention, the variants $R_1$ and $R_2$ may be selected amongst cations of a pharmaceutically acceptable base. Such cations may for example be selected from Na, K, Ca, Mg, and other organic bases as disclosed herein.

The chemical bases which are used as reagents to prepare the pharmaceutically acceptable base salts of compounds of the present invention are those which form non-toxic base salts with the herein described acidic derivatives. These particular non-toxic base salts include those derived form such pharmaceutically acceptable cations as sodium, potassium, calcium and magnesium, etc. These salts can easily be prepared by treating the compounds of the invention having at least one acidic group with an aqueous solution containing the desired pharmaceutically acceptable cation, and then evaporating the resulting solution to dryness, in some embodiments under reduced pressure. Typically, stoichiometric quantities of reagents are employed in order to ensure completeness of reaction and maximum production of yields of the desired final product (see for example "Handbook of Pharmaceutical Salts: Properties, Selection, and Use" by P. H. Stahl and C. G. Wermuth).

Compounds of the invention having both acidic and basic groups may also be obtained as internal salts (Zwitterions).

The present invention also relates to prodrug derivatives of the compounds of the invention. As known to the person skilled in the art, the term "prodrug" refers to pharmacologically inactive precursors of a drug that may be converted into its therapeutically active compounds of the invention under physiological conditions in vivo or in vitro, for example, when they undergo solvolysis, or enzymatic degradation in blood, or in cells (See as background reference: The Organic Chemistry of Drug Design and Drug Action, Academic Press, San Diego, Calif., 1992).

Within the scope of the invention, the term also encompasses any covalently bonded carriers, which release the active compound in vitro or in vivo when administered to an animal, e.g., mammals (humans) and other animals. Prodrug modifications of a compound often offer advantages of solubility, bioavailability, absorption, tissue compatibility, tissue distribution, or delayed release in the mammalian organism. While the prodrug derivatives of compounds of the invention have groups cleavable under metabolic conditions, for example, pharmaceutically acceptable esters, or amides, it is to be understood that such cleaving does not refer to cleaving of a bond between moieties G and L and/or L and Q in the general formula G-L-Q. The cleavable groups being different from G, L and Q can be cleaved enzymatically or non-enzymatically, or hydrolytically.

The prodrug may also be a reduced form, which is oxidized in vivo to the therapeutic compound.

Thus, the present invention provides compounds, enantiomers thereof, racemic mixtures thereof, salts thereof (being pharmaceutically acceptable or unacceptable), internal salts thereof, hydrates thereof, polymorphs thereof, prodrugs thereof and mixtures of any one form thereof. Any of these enantiomers, racemic mixtures, salts (being pharmaceutically acceptable or unacceptable), internal salts, hydrates, polymorphs, prodrugs and mixtures apply to any one of Compound 1 through Compound 10 and any compound of the general formulae (I) to (VII).

Pure compounds may be obtained following methods of purification as known in the art. Where the reaction product is a mixture of isomers, specific isomers may be separated by means of classical separation techniques, such as chromatographic or crystallization methods, or by other methods known in the art, such as through formation of diastereomeric salts, for example by salt formation with an enantiomerically pure chiral acid, or by means of chromatography, for example by using chromatographic materials modified with chiral ligands.

The compounds of the invention are inhibitors of one or more of matrix metalloproteinases (MMP) and one or more disintegrin and metalloproteinase (ADAM).

The compounds of the invention may also be used as inhibitors of the MMP corresponding proenzymes. As known to a person skilled in the art, the term "proenzyme" refers to a precursor or pro-form of the MMP or ADAM enzyme. Typically, the proenzyme is constituted by a propeptide part and a polypeptide part comprising the amino acid sequence of the active enzyme.

The invention provides a use of at least one compound of the invention in medicine. In some embodiments, the use is in a method for inhibiting MMP and/or ADAM (or proenzymes thereof).

The invention also provides a use of at least one compound of the invention in the preparation of a composition. In some embodiments, the composition is a pharmaceutical composition. In further embodiments, the pharmaceutical composition is for use in medicine.

In another aspect of the invention, there is provided a composition comprising at least one compound of the invention. In some embodiments, the composition is a pharmaceutical composition. In other embodiments, the pharmaceutical composition further comprises a carrier, an excipient or a diluent.

As used herein, the at least one compound of the invention is any one compound of any one of formulae (I) to (VII), including any one compound herein designated Compound 1, 1A, 2, 2A, 3, 3A, 4, 4A, 5, 5A, 6, 7, 8, 8A, 8R, 8S, 9 and Compound 10.

In some embodiments of the above aspects, the compounds of the invention are inhibitors or used in inhibiting (in some embodiments as comprised in a pharmaceutical composition) at least MMP, or a proenzyme thereof, as known in the art. In some embodiments, said MMP selected from MMP-1, MMP-2, MMP-3, MMP-7, MMP-8, MMP-9, MMP-10, MMP-11, MMP-12, MMP-13, MMP-14, MMP-15, MMP-16, MMP-17, MMP-18, MMP-19, MMP-20, MMP-21, MMP-23A, MMP-23B, MMP-24, MMP-25, MMP-26, MMP-27 and MMP-28. In other embodiments, said MMP is selected from MMP-1, MMP-2, MMP-3, MMP-8, MMP-9, MMP-12 and MMP-13. In further embodiments, said MMP is selected from MMP-2 and MMP-9.

In further embodiments, said inhibitor is a compound selected from compounds herein designated Compound 1, 2, 3, 4 and 5 and said MMP is selected from MMP-2, MMP-3, MMP-12 and MMP-13.

In some embodiments, the inhibitor is Compound 1 and the MMP is selected from MMP-2, MMP-12 and MMP-13.

In other embodiments, the inhibitor is Compound 2 and the MMP is selected from MMP-2, MMP-3 and MMP-13.

In further embodiments, the inhibitor is Compound 3 and the MMP is selected from MMP-2 and MMP-13.

In still other embodiments, the inhibitor is Compound 4 and the MMP is selected from MMP-2, MMP-12 and MMP-13.

In other embodiments, the inhibitor is Compound 5 and the MMP is selected from MMP-2 and MMP-13.

In further embodiments, said inhibitor is a compound selected from compounds herein designated Compound 8, 8R, 8S, and 10 and said MMP is selected from MMP-2, MMP-3, MMP-8, MMP-9 and MMP-12.

In some embodiments, said inhibitor is Compound 8 (a racemate of Compounds 8R and 8S) and said MMP is selected from MMP-2, MMP-8, MMP-9 and MMP-12.

In some embodiments, said inhibitor is Compound 8R and said MMP is selected from MMP-2, MMP-8 and MMP-12.

In further embodiments, said inhibitor is Compound 8S and said MMP is MMP-2.

In still other embodiments, said inhibitor is Compound 10 and said MMP is MMP-2.

In other embodiments of any of the above aspects, the compounds of the invention are inhibitors or used in inhibiting (in some embodiments as comprised in a pharmaceutical composition) at least one ADAM, or a proenzyme thereof, as known in the art. In some embodiments, said ADAM is selected from ADAM-10, ADAM-17 (tumor necrosis factor-a-converting enzyme, TACE), ADAMTS-2, ADAMTS-5 and ADAMTS-13. In some embodiments, said ADAM is ADAM-17 (TACE).

In some embodiments, said inhibitor is selected from Compounds 1, 5, 6, 7 and 8 and said ADAM is TACE.

Thus, the invention also provides a pharmaceutical composition for treating and/or preventing a disease or disorder treatable and/or preventable by inhibiting at least one MMP and/or ADAM, as disclosed herein.

As disclosed herein, the compounds of the invention and compositions comprising same are inhibitors or inhibitor compositions of an MMP or ADAM or proenzymes thereof. As known in the art, the term "inhibitor" or any lingual variation thereof, refers to the ability of a compound or a composition comprising same to restrict, limit, hinder, prevent or completely arrest the activity of the MMP and/or ADAM enzyme(s) and/or restrict, limit, hinder, prevent or completely arrest the transformation of the proenzyme to the respective active form. In some embodiments, the compound or composition according to the invention are used for degrading or denaturizing the extracellular matrix components.

The inhibitor may also be an endogenous tissue inhibitor of metalloproteinases, known to be involved in physiological/biological functions including the inhibition of active matrix metalloproteinases, regulation of proenzyme activation, cell growth, and the modulation of angiogenesis.

The inhibitory activity of a MMP/ADAM inhibitor of the invention may be assessed by any method suitable for determining inhibitory activity of a compound with respect to an enzyme. Such methods are described in standard textbooks of biochemistry.

The pharmaceutical composition of the invention comprise one or more compound of any one of formula (I) to (VII), optionally with one or more carrier, excipients or diluent. The pharmaceutically acceptable carriers, described herein, are well-known to those who are skilled in the art and are readily available to the public. It is preferred that the pharmaceutically acceptable carrier be one which is chemically inert to the active compounds and one which has no detrimental side effects or toxicity under the conditions of use.

The composition of the invention may be adapted as a composition for any type of immediate or sustained release.

The composition of the invention may be formulated to include in addition to one or more of the active compounds of the invention at least one pharmaceutically active additive.

The compositions of the invention may be formulated by mixing at least one active compound of the invention with said carrier, excipient or diluent. The mixing of the components may be carried in accordance with any one method known in the art.

The choice of a carrier will be determined in part by the particular compound of the invention, as well as by the particular method used to administer the composition comprising the compound. Accordingly, there is a wide variety of suitable formulations of the pharmaceutical composition of the present invention. The following formulations for oral, topical, transdermal, aerosol, parenteral, subcutaneous, intravenous, intramuscular, interperitoneal, rectal and vaginal administration are merely exemplary and are in no way limiting.

In some embodiments, the pharmaceutical composition of the invention is adapted for oral administration.

Formulations suitable for oral administration may consist of (a) liquid solutions, such as an effective amount of the compound dissolved in diluents, such as water, saline, or orange juice; (b) capsules, sachets, tablets, lozenges, and troches, each containing a predetermined amount of the active ingredient, as solids or granules; (c) powders; (d) suspensions in an appropriate liquid; and (e) suitable emulsions. Liquid formulations may include diluents, such as water and alcohols, for example, ethanol, benzyl alcohol, and the polyethylene alcohols, either with or without the addition of a pharmaceutically acceptable surfactant, suspending agent, or emulsifying agent. Capsule forms can be of the ordinary hard- or soft-shelled gelatin type containing, for example, surfactants, lubricants, and inert fillers, such as lactose, sucrose, calcium phosphate, and corn starch. Tablet forms can include one or more of lactose, sucrose, mannitol, corn starch, potato starch, alginic acid, microcrystalline cellulose, acacia, gelatin, guar gum, colloidal silicon dioxide, talc, magnesium stearate, calcium stearate, zinc stearate, stearic acid, and other excipients, colorants, diluents, buffering agents, disintegrating agents, moistening agents, preservatives, flavoring agents, and pharmacologically compatible carriers. Lozenge forms can comprise the active ingredient in a flavor, usually sucrose and acacia, as well as pastilles comprising the active ingredient in an inert base, such as gelatin and glycerin, or sucrose and acacia, emulsions, gels, and the like containing, in addition to the active ingredient, such carriers as are known in the art.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that include suspending agents, solubilizers, thickening agents, stabilizers, and preservatives. The compound can be administered in a physiologically acceptable diluent in a pharmaceutical carrier, such as a sterile liquid or mixture of liquids, including water, saline, aqueous dextrose and related sugar solutions, an alcohol, such as ethanol, iso-propanol, or hexadecyl alcohol, glycols, such as propylene glycol or polyethylene glycol, glycerol ketals, such as 2,2-dimethyl-1,3-dioxolane-4-methanol, ethers, such as poly(ethyleneglycol) 400, an oil, a fatty acid, a fatty acid ester or glyceride, or an acetylated fatty acid glyceride with or without the addition of a pharmaceutically acceptable surfactant, such as a soap or a detergent, suspending agent, such as pectin, carbomers, methylcellulose, hydroxypropylmethylcellulose, or carboxymethyl cellulose or emulsifying agents and other pharmaceutical adjuvants.

Oils, which can be used in parenteral formulations, include petroleum, animal, vegetable, or synthetic oils. Specific examples of oils include peanut, soybean, sesame, cottonseed, corn, olive, petrolatum, and mineral. Suitable fatty acids for use in parenteral formulations include oleic acid, stearic acid, and isostearic acid. Ethyl oleate and isopropyl myristate are examples of suitable fatty acid esters. Suitable soaps for use in parenteral formulations include fatty alkali metal, ammonium, and triethanolamine salts, and suitable detergents include (a) cationic detergents such as, for example, dimethyl dialkyl ammonium halides, and alkyl pyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxy-ethylenepolypropylene copolymers, (d) amphoteric detergents such as, for example, alkyl-β-aminopriopionates, and 2-alkyl-imidazoline quaternary ammonium salts, and (3) mixtures thereof.

The parenteral formulations will typically contain from about 0.5 to about 25% by weight of the compound(s) of the invention in solution. Suitable preservatives and buffers can be used in such formulations. In order to minimize or eliminate irritation at the site of injection, such compositions may contain one or more nonionic surfactants having a hydrophile-lipophile balance (HLB) of from about 12 to about 17. The quantity of surfactant in such formulations ranges from about 5 to about 15% by weight. Suitable surfactants include polyethylene sorbitan fatty acid esters, such as sorbitan monooleate and the high molecular weight adducts of ethylene oxide with a hydrophobic base, formed by the condensation of propylene oxide with propylene glycol. The parenteral formulations can be presented in unit-dose or multi-dose sealed containers, such as ampoules and vials, and can be stored in a freeze-dried (lyophilized) condition requiring only the addition of the sterile liquid carrier, for example, water, for injections, immediately prior to use. Extemporaneous injection solutions and suspensions can be prepared from sterile powders, granules, and tablets of the kind previously described.

The requirements for effective pharmaceutical carriers for injectable compositions are well known to those of ordinary skill in the art. See Pharmaceutics and Pharmacy Practice, J.B. Lippincott Co., Philadelphia, Pa., Banker and Chalmers, eds., pages 238-250 (1982), and ASHP Handbook on Injectable Drugs, Toissel, 4th ed., pages 622-630 (1986).

The invention also provides a method for inhibiting the activity of an MMP and/or ADAM enzyme in vitro or in vivo, said method comprising contacting a sample (e.g., a tissue sample, a blood sample, animal body including human) containing or suspected to be containing an MMP and/or ADAM enzyme(s) with an effective amount of a compound of the invention or with a composition comprising same.

The invention also concerns a method for delivering (e.g., selective delivery) an inhibitor of the invention to an extracellular space in a body tissue (in vitro sample or in vivo in the body of a subject), said method comprising contacting said tissue with a compound or composition according to the invention. In some embodiments, the tissue is an animal body. As used herein, the "extracellular space" is the space outside the plasma membrane which is typically occupied by fluid. The method of the invention is, thus, directed to the delivery of the compound of the invention selectively into this space and substantially not into the cells.

In another aspect, the invention provides a method for inhibiting the activity of a MMP and/or ADAM enzyme in a subject, to thereby treat or prevent a disease or disorder in said subject, said disease or disorder being associated with the enzyme activity, said method comprising administering an effective amount of a compound or composition according to the invention to a subject suffering or having a predisposition (genetic, environmental or otherwise) to suffer from such a disease or disorder.

Still further, the invention provides a method for treating or preventing a disease or disorder associated with the activity of MMP and/or ADAM in a subject, said method comprising administering to said subject an effective amount of a compound or composition according to the invention.

The disease or disorder associated with the activity of MMP and/or ADAM enzyme(s) is selected from inflammatory and allergic diseases; cancers, such as solid tumors or tumor metastasis or invasion; disease associated with uncontrolled degradation of the extracellular matrix, such as osteoarthritis; bone resorptive disease (e.g., osteoporosis and Paget's disease); diseases associated with aberrant angiogenesis; the enhanced collagen remodelling associated with diabetes, periodontal disease (e.g., gingivitis), corneal ulceration, ulceration of the skin, post-operative conditions (e.g., colonic anastomosis) or dermal wound healing; demyelinating diseases of the central and peripheral nervous systems (e.g., multiple sclerosis); Alzheimer's disease; extracellular matrix remodeling; cardiovascular diseases such as myocardial infarction, congestive heart failure, restenosis or atherosclerosis; asthma; rhinitis; and chronic obstructive pulmonary diseases (COPD).

In some embodiments, the disease or disorder is inflammation. Non-limiting examples of inflammatory disease or disorders treatable or preventable by inhibitors of MMP and/or ADAM enzyme(s) include inflammations of the joint, such as rheumatoid arthritis, osteoarthritis and gout; inflammation of the gastro-intestinal tract, such as inflammatory bowel disease, ulcerative colitis and gastritis; and inflammation of the skin such as psoriasis, eczema, and dermatitis.

In some embodiments, the disease or disorder is cancer. Non-limiting examples of cancers treatable or preventable by inhibitors of MMP and/or ADAM enzyme(s) include any malignant condition. In most general terms, the cancers treatable or preventable by inhibitors of MMP and/or ADAM of the invention, are selected amongst blastoma, carcinoma, lymphoma, leukemia, sarcoma, mesothelioma, glioma, germinoma, choriocarcinoma, melanoma, glioblastoma, lymphoid malignancies and any other neoplastic disease or disorder.

Non-limiting examples of cancers are squamous cell cancer (e.g. epithelial squamous cell cancer), lung cancer including small-cell lung cancer, non-small cell lung cancer, adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, as well as head and neck cancer.

In some other embodiments, said cancer is a solid cancer, selected in a non-limiting manner from breast cancer, prostate cancer, sarcomas and skin cancer.

In some embodiments, the solid cancer is melanoma.

In further embodiments, the disease or disorder is selected amongst such which are treatable or preventable by decreasing the amount of TNF-α and such conditions as inflammatory conditions, e.g., autoimmune conditions such as rheumatoid arthritis, ankylosing spondylitis, Crohn's disease, psoriasis and refractory asthma, infectious and parasitic diseases or states of shock in which endogenous TNF-α is released, as well as cachexia, GVHR, and Adult Respiratory Distress Symptom (ARDS).

In some embodiments, the inhibitors of the invention are selected to specifically inhibit a disease-related MMP or ADAM enzyme. In some embodiments, the disease or disorder is MMP-2-associated disease or disorder selected from inflammatory and allergic diseases, such as multiple sclerosis, inflammation of the joint (e.g., rheumatoid arthritis, osteoarthritis and gout), inflammation of the gastro-intestinal tract (e.g., inflammatory bowel disease, ulcerative colitis and gastritis), inflammation of the skin (e.g., psoriasis, eczema, dermatitis); cancers and tumor metastasis or invasion; disease associated with uncontrolled degradation of the extracellular matrix such as osteoarthritis; in bone resorptive disease (e.g., osteoporosis and Paget's disease); diseases associated with aberrant angiogenesis; the enhanced collagen remodelling associated with diabetes, periodontal disease (e.g., gingivitis), corneal ulceration, ulceration of the skin, post-operative conditions (e.g., colonic anastomosis) and dermal wound healing; demyelinating diseases of the central and peripheral nervous systems (e.g., multiple sclerosis); Alzheimer's disease; extracellular matrix remodelling observed in cardiovascular diseases such as myocardial infarction, congestive heart failure, restenosis and atherosclerosis; asthma; rhinitis; and chronic obstructive pulmonary diseases (COPD).

In some embodiments, the MMP-2-associated disease or disorder is cancer. In some further embodiments, said cancer is solid tumor. In further embodiments, said cancer is melanoma.

In some embodiments, the disease or disorder is MMP-12-associated disease or disorder, such as COPD pathogenesis.

In some embodiments, the disease or disorder is MMP-9-associated disease or disorder selected amongst cardiovascular diseases.

In some embodiments, the disease or disorder is MMP-13-associated disease or disorder selected from metastasis involving diseases such as invasive breast cancer lesions and malignant epithelia growth in skin carcinogenesis, as well as various diseases involving COPD and bone remodeling, such as in destructive joint diseases as rheumatoid and osteo-arthritis.

In some embodiments, the disease or disorder is TACE-associated disease or disorder selected amongst such which are treatable or preventable by decreasing the amount of TNF-a and such conditions as inflammatory conditions, e.g., autoimmune conditions such as rheumatoid arthritis, ankylosing spondylitis, Crohn's disease, psoriasis and refractory asthma, infectious and parasitic diseases or states of shock in which endogenous TNF-α is released, as well as cachexia, GVHR, and Adult Respiratory Distress Symptom (ARDS).

The "effective amount" for purposes herein is determined by such considerations as may be known in the art. The amount of the inhibitor or composition of the invention must be effective to achieve the desired therapeutic effect as described above, i.e. inhibition of at least one of the MMP and/or ADAM enzymes, depending, inter alia, on the type and severity of the disease to be treated and the treatment regime. The effective amount is typically determined in appropriately designed clinical trials (dose range studies) and the person versed in the art will know how to properly conduct such trials in order to determine the effective amount. As generally known, an effective amount depends on a variety of factors including the affinity of the inhibitor to the enzyme, its distribution profile within the body, a variety of pharmacological parameters such as half life in the body, on undesired side effects, if any, on factors such as age and gender, etc.

The terms "treatment" and/or "prevention" or any lingual variation of either or both terms, as used herein refer to the administering of a therapeutic amount of the inhibitor compound or composition of the present invention which is effective to ameliorate undesired symptoms associated with a disease, as defined herein, prevent the manifestation of such symptoms before they occur, slow down the progression of the disease, slow down the deterioration of symptoms, enhance the onset of remission period, slow down the irreversible damage caused in the progressive chronic stage of the disease, delay the onset of said progressive stage, lessen the severity or cure the disease, improve survival rate or more rapid recovery, prevent the disease form occurring or a combination of two or more of the above.

In a further aspect, the invention provides a diagnostic method for determining the presence and/or concentration of at least one MMP and/or ADAM enzyme(s) in a sample. In the diagnostic method, a sample suspected of or known to contain a certain concentration (e.g., detectable) of at least one MMP and/or ADAM is contacted with at least one compound of the invention for a time period and under conditions which enable association (interaction, and in some embodiments also inhibition) to said enzyme by said at least one compound of the invention, wherein said at least one compound is previously detectably-labeled by a marker, as known in the art.

The compound of the invention used in the diagnostic method of the invention may be labeled by at least one marker group which may be a radioactive isotope, a dye, a magnetic bead, or other detectable group. Non-limiting examples of detectable markers include a radioactive label, a fluorescent label, a chemiluminescent label, a chromophoric label, a phosphorescent label, an electronic label, a colored bead, a physical label, or a ligand.

Following association or deactivation of the enzyme by the labeled compound of the invention, the association or inhibition is detected by at least one change in a measurable parameter associated with the label. The measurable parameter may be selected from any such parameter characteristic of the label employed and the method used for its detection.

The measurable parameter may be used for quantitative and/or qualitative measurements. Where the diagnostic method is employed for the purpose of determining the presence of the enzyme, any change in the measurable parameter of the marker, in comparison to the a control, e.g., the inhibition amounts detected to calibration curve, may provide the indication that a certain concentration of the MMP and/or ADAM enzyme(s) is present in the sample. Where the diagnostic method is employed for quantitative purposes, the amount or degree of change in the detectable parameter measured, as compared to a calibration curve, may provide such quantitative determination.

It should be stressed that for some of the embodiments recited herein, e.g., for quantitative measurement in vitro, in order to achieve an accurate measurement of the amount of the MMP and/or ADAM enzyme(s) present in the sample, the diagnostic method may also involve the inclusion of a substrate of said enzyme(s).

In some embodiments, the substrate is previously detectably-labeled by a marker, as disclosed above. The amount or degree of change in the detectable parameter measured, as compared to a calibration curve may provide such quantitative determination.

The diagnostic method may be used to analyze a sample in vitro or to determine the location and characteristics of a pathological condition, in vivo in a subject, wherein the condition is characterized with an accumulation of the enzyme.

In another aspect of the invention there is provided a kit (or a commercial package) comprising at least one compound of the invention and instructions for use. The kit may comprise any number of containers (vials, receptacles) and further optionally at least one solvent or diluent for dissolving the at least one compound contained therein.

BRIEF DESCRIPTION OF THE FIGURES

In order to understand the invention and to see how it may be carried out in practice, embodiments will now be described, by way of non-limiting example only, with reference to the accompanying drawings, in which.

DETAILED DESCRIPTION OF THE INVENTION

Figure 1:
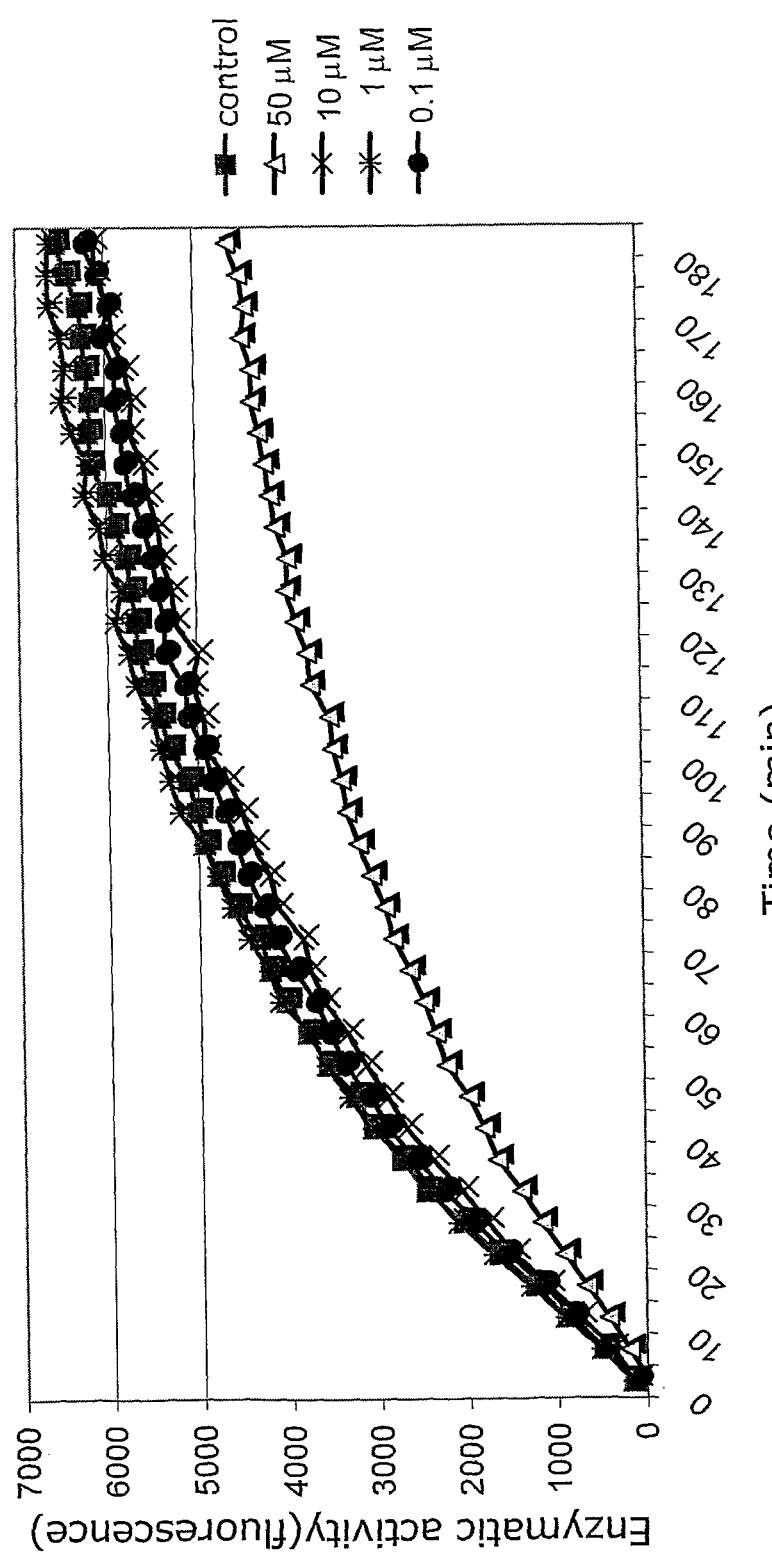
FIG. 1 demonstrates the effect Compound 1 of the invention on MMP-2.
Figure 2:
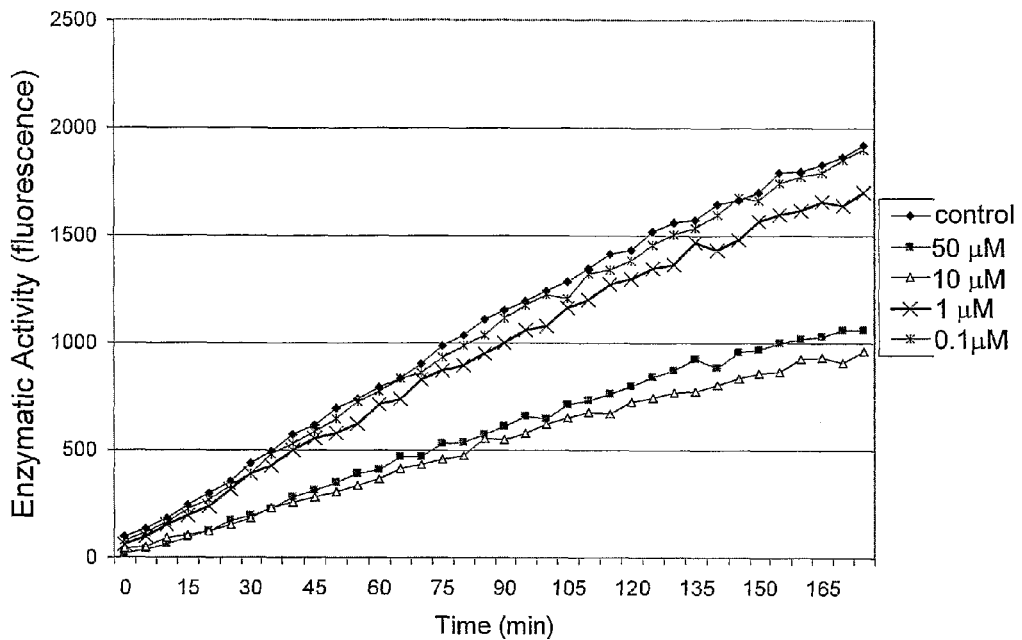
FIG. 2 demonstrates the effect of Compound 4 on MMP-2.
Figure 3:
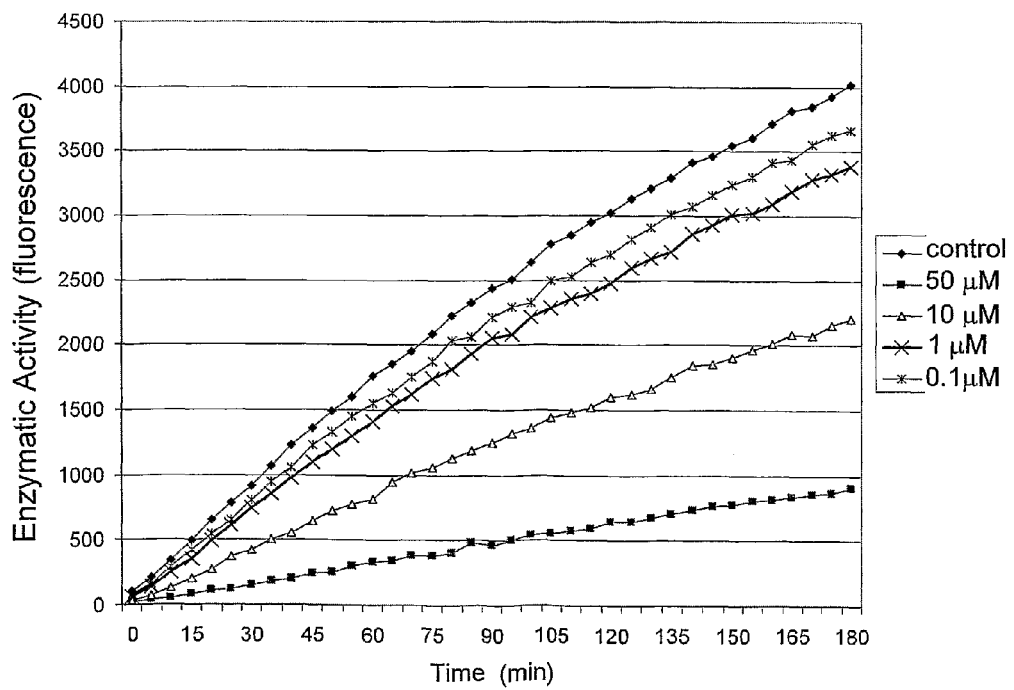
FIG. 3 demonstrates the effect of Compound 5 on MMP-2.
Figure 4A:
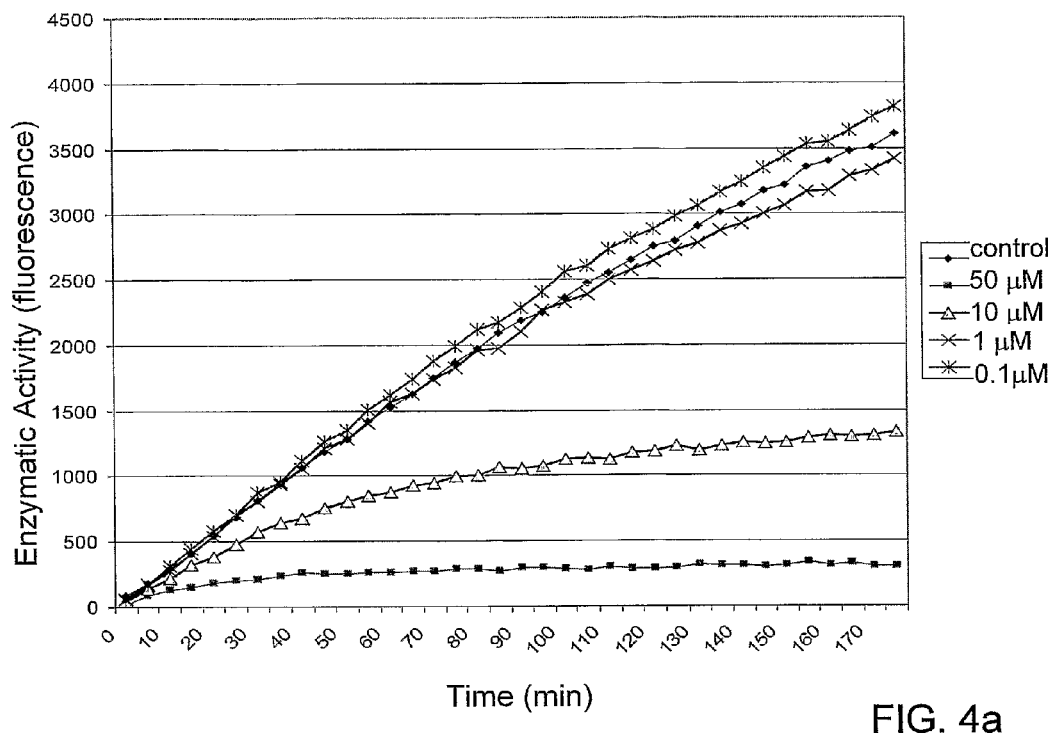
FIG. 4A—effect on MMP-2.
Figure 4B:
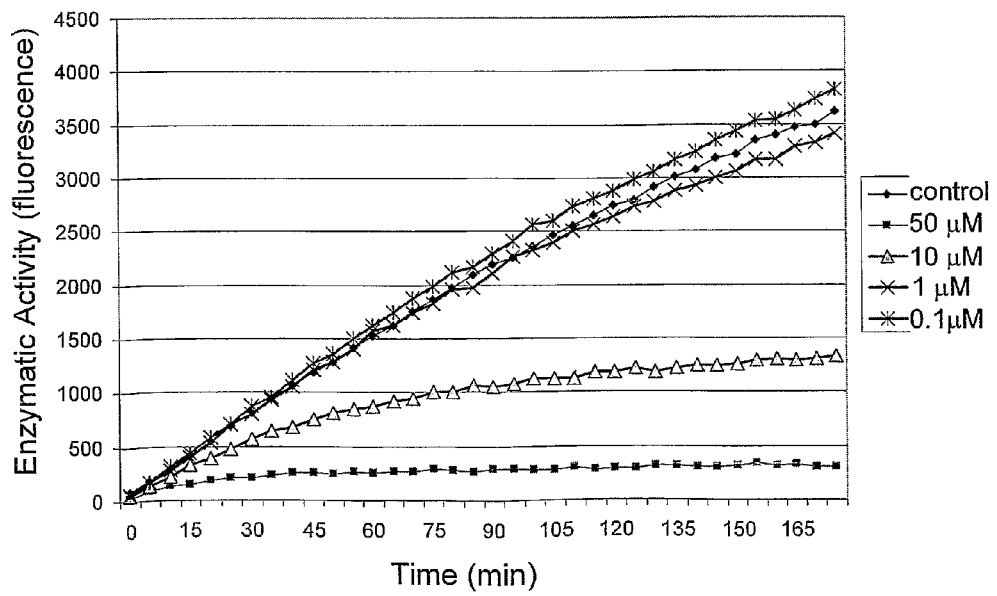
FIG. 4B effect on MMP-9, FIG. 4C effect on MMP-3, FIG. 4D effect on MMP-8, and FIG. 4E effect on TACE.
Figure 4C:
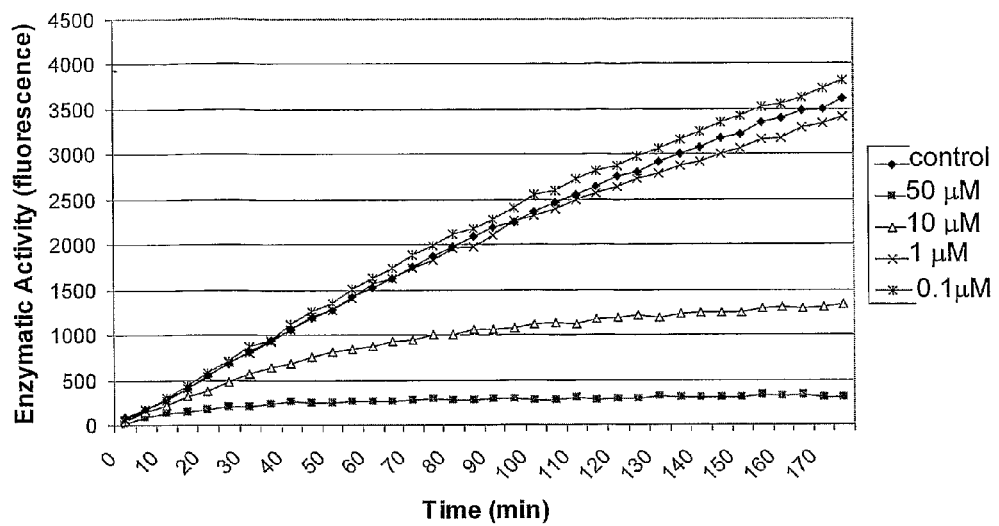
FIG. 4 demonstrates the effect of Compound 8 on various MMPS and ADAMs.
Figure 4D:
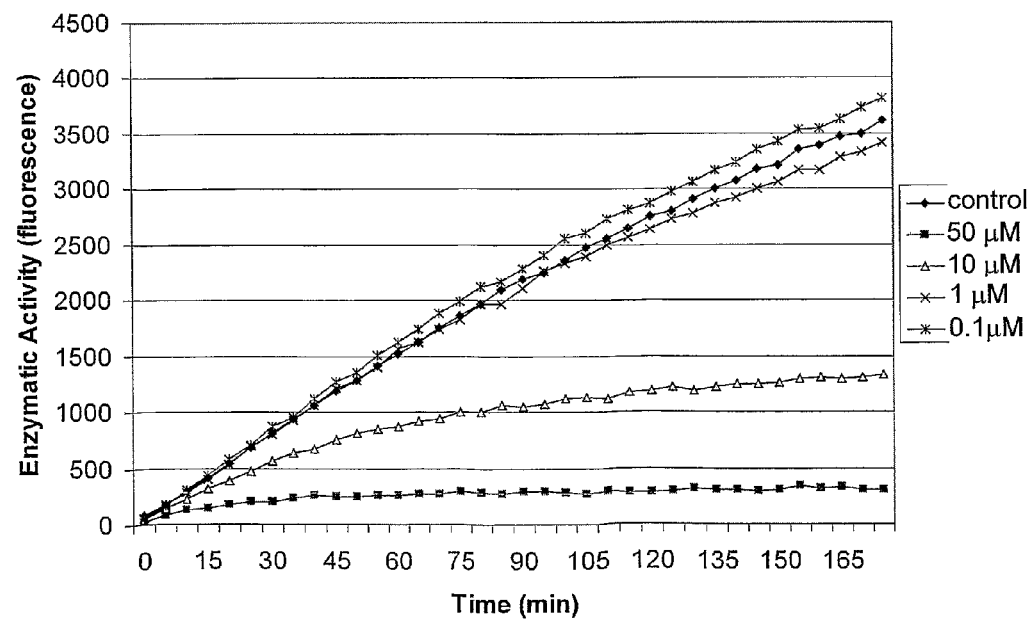
Figure 4E:
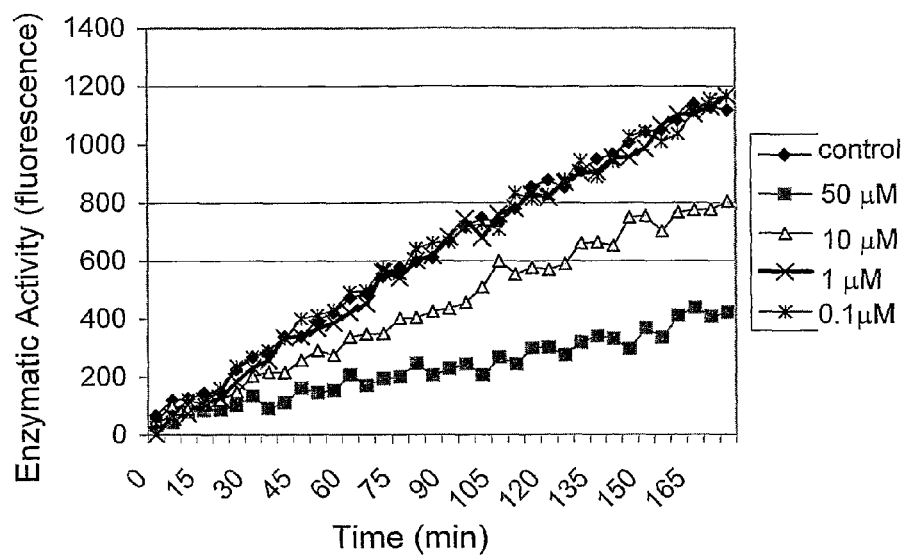

The present invention concerns matrix metalloproteinase inhibitors of increased affinity based on carbamoylphosphonic acids. The present invention thus concerns, in some embodiments and as indicated above, also compounds of the general formulae 1, 2 and 3, shown below, as well as their acidic forms and their pharmaceutically acceptable salts with inorganic as well as organic bases.

In the structures 1, 2, 3 shown below, X may be H or a substituent selected from Cl, F, $CF_3$, $CF_3O$, $CH_3$ $NH_2$, $NR_4H$, $NR_4R_5$ $NHCOR_4$ ($R_4$=lower alkyl, aryl); in some embodiments, F, Cl, $CF_3$, $CF_3O$, and $CH_3$ at any position in the ring, in further embodiments, at the meta or para position, and in yet other embodiments at the para position. In $NR_4R_5$, $R_4$ and $R_5$ together may form a chain of $CH_2$ groups forming a ring that includes the N atom.

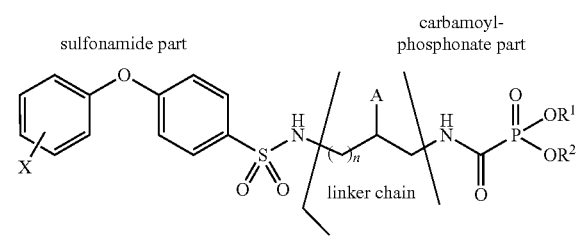

1
sulfonamide part    carbamoyl-phosphonate part

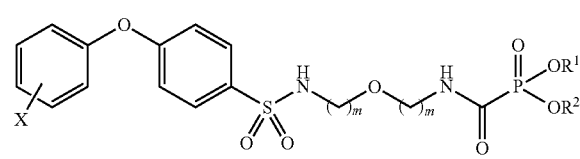

2

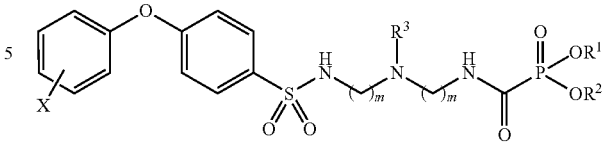

3

$R_1$ and $R_2$ may be different or identical; they may be H or a cation of a pharmaceutically acceptable base, as defined herein, but not restricted to those that appear in, the "Handbook of Pharmaceutical Salts: Properties, Selection, and Use" by P. H. Stahl and C. G. Weimuth.

n=0-7 (in structure 1). The total number of carbons (or the $CH_2$ groups) in the "linker chain" connecting the sulfonamide group with the carbamoylphosphonic group may be 2-9 (where n is 1-7).

m=2-4 (in structures 2 and 3).

The carbon atoms in the "linker chain" may carry primary, secondary or tertiary (cyclic or acyclic), amino group substituents (marked A) in various positions on the chain (see for example A in structure 1).

One of the $CH_2$ groups of the "linker chain" may be replaced by an O atom or an $NR_3$ group ($R_3$=H or an alkyl group) shown in structures 2 and 3, respectively.

The compounds of any of the above formula 1, 2 or 3 may be used as MMP inhibitors and more specifically as inhibitors of MMP-2, inhibitors of MMP-9, MMP-12, MMP-13 and of TACE.

The present invention further concerns pharmaceutical compositions comprising a pharmaceutically acceptable carrier and as an active ingredient at least one of the compounds of structure 1, 2 or 3 or combinations thereof.

The compositions may be used to treat a disease wherein a therapeutically beneficial effect may be evident by the inhibition of at least one MMP. In some embodiments, the inhibition is of MMP-2. MMP-9, MMP-12, MMP-13 or TACE.

Examples of such diseases, where a therapeutically beneficial effect can be evident from MMP-2 inhibition are: inflammatory and allergic diseases such as, inflammation of the joint (especially rheumatoid arthritis, osteoarthritis and gout), inflammation of the gastro-intestinal tract (especially inflammatory bowel disease, ulcerative colitis and gastritis), inflammation of the skin (especially psoriasis, eczema, dermatitis); in tumor metastasis or invasion; in disease associated with uncontrolled degradation of the extracellular matrix such as osteoarthritis; in bone resorptive disease (such as osteoporosis and Paget's disease); in diseases associated with aberrant angiogenesis; the enhanced collagen remodelling associated with diabetes, periodontal disease (such as gingivitis), corneal ulceration, ulceration of the skin, post-operative conditions (such as colonic anastomosis) and dermal wound healing; demyelinating diseases of the central and peripheral nervous systems (such as multiple sclerosis); Alzheimer's disease; extracellular matrix remodelling observed in cardiovascular diseases such as myocardial infarction, congestive heart failure, restenosis and atherosclerosis; asthma; rhinitis; and chronic obstructive pulmonary diseases (COPD).

In some embodiments, the disease in cancer, and in further embodiments solid tumors. In other embodiments, said cancer is melanoma.

Examples of diseases where a therapeutically beneficial effect may be evident by MMP-12 inhibition are in the COPD pathogenesis.

Examples of diseases where a therapeutically beneficial effect may be evident by MMP-9 inhibition are in the cardiovascular diseases.

Examples of diseases where a therapeutically beneficial effect may be evident by MMP-13 inhibition includes metastasis involving diseases such as invasive breast cancer lesions and in malignant epithelia growth in skin carcinogenesis) as well as in various diseases involving bone remodeling such as in destructive joint diseases such as rheumatoid and osteo-arthritis.

Examples of diseases where a therapeutically beneficial effect may be evident by TACE inhibition are all disease which may benefit by the decrease in the amount of TNF-alpha and in particular inflammatory conditions such as autoimmune conditions for example rheumatoid arthritis, ankylosing spondylitis, Crohn's disease, psoriasis and refractory asthma, infectious and parasitic diseases or states of shock in which endogenous TNF-α is released, as well as cachexia, GVHR, ARDS (Adult Respiratory Distress Symptom).

By another aspect, the present invention is based on the observation that carbamoylphosphonic acids in general, based on their volume of distribution, reside almost exclusively in the extracellular space and do not enter cells.

Thus, by another aspect the present invention concerns a method for selectively delivering a carbamoylphosphonic acid based MMP inhibitor to the extracellular space in the body of a subject, while substantially not entering into cells, the method comprising: administering to the subject an MMP inhibiting carbamoylphosphonic acid or a salt thereof.

In some embodiments, the inhibitor is administered orally.

The term "MMP inhibitors" refers to any inhibitor of an enzyme of the MMP family and in particular refers to MMP-2, MMP-9, MMP-12, MMP-13 and TACE inhibitors.

In the following Table 1, for each of the specifically designated Compound 1 to 9 of the invention the designation used in the biological assays is provided.

TABLE 1

Designations of Compounds of the invention.

| Compound 1 | JS-268 |
| Compound 2 | JS-325 |
| Compound 3 | JS-343 |
| Compound 4 | JS-389 |
| Compound 5 | JS-403 |
| Compound 6 | TCH-18 |

TABLE 1-continued

Designations of Compounds of the invention.

| Compound 7 | TCH-23 |
| Compound 8 | JS-489 |
| Compound 8R | AV-70(R) |
| Compound 8S | AV-64(S) |
| Compound 9 | JS-426 |

The results of a preliminary biological evaluation of the compounds of the invention are summarized in Tables 2, 3 and 4 and FIGS. 1 to 5.

All compounds showed inhibition for a period of at least 3 hours, as compared to previously reported MMP inhibitors. Previously, it has been established that cis-2-aminocyclohexycarbamoyl phosphonic acid (cis-ACCP), listed for the purpose of comparison in Tables 2 and 3 as "control", was an effective nontoxic, in vivo active antimetastatic compound. However, it was found that cis-ACCP inhibits MMP-2 for the period of only about 30 minutes. As demonstrated herein, the period of inhibition was prolonged, in comparison to such compounds as cis-ACCP, while maintaining the inhibitory activity and without inducing further toxicity. In the study leading to the subject invention, it was determined that the inhibitory effect could be, and in fact was prolonged by substituting carbamoylphosphonic functionality with aromatic ring functionality as in the compounds of the invention.

Compound 1, also referred to as JS-268-1 was found active (both in vitro and in vivo). In spite of the relatively weak inhibition constant determined in vitro, Compound 1 exhibited significant in vivo potency, in a murine melanoma model. Further analogues of Compound 1 have been prepared and demonstrated to have inhibitory function on MMP and/or ADAM enzyme activity.

Several and exemplary analogues of Compound 1 are listed in Tables 2 and 3. As demonstrated in these Tables, the presence of an amine group in the linker moiety connecting the phenoxybenzenesulfonamide and carbamoylphosphonic acid moieties affected the inhibitory activity. The incorporation of a secondary amine in the linker chain as in Compound 10 (JS-426) reduced the inhibitory potency, while the addition of a primary amine group, as a pendant group on the linker alkylene moiety, as in Compound 8 (JS-489), and enantiomers thereof, generated an inhibitor with a broad spectrum of activity of considerable potency and high (>3 h) affinity to all the enzymes inhibited.

TABLE 2

Potency and selectivity profiles of carbamoylphosphonate MMP inhibitors of the invention.

| Symbol | Linker Moiety* | $IC_{50}$ (μM) on MMP-2 | $IC_{50}$ (μM) on MMP-3 | $IC_{50}$ (μM) on MMP-8 | $IC_{50}$ (μM) on MMP-9 | $IC_{50}$ (μM) on MMP-12 | $IC_{50}$ (μM) on MMP-13 | $IC_{50}$ (μM) on TACE |
|---|---|---|---|---|---|---|---|---|
| YK-162 | control | 4 | >100 | >100 | 20 | >100 | >100 | >100 |
| JS-268 | G—$(CH_2)_2$—Q | 15 | >100 | >100 | >100 | 60 | 55 | 6 |
| JS-325 | G—$(CH_2)_3$—Q | 10 | 35 | >100 | >100 | >100 | 25 | >100 |
| JS-343 | G—$(CH_2)_4$—Q | 7 | >100 | >100 | >100 | >100 | 25 | >100 |
| JS-389 | G—$(CH_2)_5$—Q | 5 | >100 | >100 | >100 | 80 | 60 | >100 |
| JS-403 | G—$(CH_2)_6$—Q | 5 | >100 | >100 | >100 | >100 | 80 | 20 |
| JS-489 | G—$CH_2CH(NH_2)CH_2$—Q | 15 | >100 | 12 | 12 | 15 | >100 | 12 |
| AV-64(S) | G—$CH_2CH(NH_2)CH_2$—Q | 15 | nd | >100 | >100 | >100 | >100 | >100 |
| AV-70(R) | G—$CH_2CH(NH_2)CH_2$—Q | 20 | >100 | 15 | >100 | 12 | >100 | >100 |
| JS-426-1 | G—$(CH_2)_2NH(CH_2)_2$—Q | 20 | >100 | >100 | >100 | nd | nd | >100 |
| TCH-18 | G—$(CH_2)_7$—Q | >100 | >100 | >100 | >100 | >100 | >100 | 22 |
| TCH-23 | G—$(CH_2)_8$—Q | >100 | >100 | >100 | >100 | >100 | >100 | 17 |

*G is a phenoxybenzenesulfonamide moiety as defined herein, and Q is the carbamoylphosphonic acid moiety, as defined herein. The control is cis-ACCP: cis-2-aminocyclohexylcarbamoyl phosphonic acid.

TABLE 3

Potency and selectivity profiles of carbamoylphosphonate MMP inhibitors of the invention.

| Symbol | Linker Moiety* | % Invasion-Inhibition by 50 μM drug | Duration of inhibitory effect (minutes) |
|---|---|---|---|
| YK-162 | control | 15 | <30 |
| JS-268 | G—(CH$_2$)$_2$—Q | 70 | >180 |
| JS-325 | G—(CH$_2$)$_3$—Q | 49 | >180 |
| JS-343 | G—(CH$_2$)$_4$—Q | 60 | >180 |
| JS-389 | G—(CH$_2$)$_5$—Q | 62 | >180 |
| JS-403 | G—(CH$_2$)$_6$—Q | 77 | >180 |
| JS-489 | G—CH$_2$CH(NH$_2$)CH$_2$—Q | nd | >180 |
| AV-64(S) | G—CH$_2$CH(NH$_2$)CH$_2$—Q | >100 | >180 |
| AV-70(R) | G—CH$_2$CH(NH$_2$)CH$_2$—Q | >100 | >180 |
| JS-426-1 | G—(CH$_2$)$_2$NH(CH$_2$)$_2$—Q | nd | >180 |
| TCH-18 | G—(CH$_2$)$_7$—Q | nd | >180 |
| TCH-23 | G—(CH$_2$)$_8$—Q | nd | >180 |

*G is the phenoxybenzenesulfonamide moiety, as defined herein, and Q is the carbamoylphosphonic acid moiety, as defined herein. The control is cis-ACCP: cis-2-aminocyclohexylcarbamoylphosphonic acid.

While the IC$_{50}$ values for Compound 1 (JS-268) and Compounds 4 and 5 (JS-389 and JS-403) differ by a factor of 3, their ability to inhibit invasion and their in vivo efficacies (not shown for Compound 1—JS-268) are nearly identical.

Synthesis of Compounds of the Invention

The synthetic approaches used for preparing the various compounds of the invention are presented in the Schemes provided in the following detailed experimental procedures.

The syntheses of the compounds of the invention having methylene group linkers are based on α,ω-diamines. In some compounds of the invention, such as Compound 1, the phosphonoformyl group was attached first to one end of the diamine and the phenoxybenzenesulfonamide group was attached later. In the case of the higher homologs having longer linker moieties, the order of the two steps was reversed. The synthesis of Compounds of the invention having a nitrogen atom, e.g., an amine group in the alkylene linker moiety, are based on diethylenetriamine and 1,3-diamino-2-propanol.

Compound 1: 1-[4-phenoxybenzenesulfonamido]-2-[phosphonoformamido]ethane (JS-268-1), Scheme 1 a) 1-Boc-amino-2-[diisopropylphosphonoformamido]ethane

To a solution of 1,2-ethanediamine (24 ml, 0.36 mol) in 25 ml MeCN was added slowly diisopropyl ethyl phosphonothiolformate (PTF-P, 8.97 g, 35.3 mmol) in 50 ml MeCN. After the addition was completed, the mixture was stirred for 1.5 h at room temperature. The reaction mixture was monitored by $^{31}$P NMR. The solvent was evaporated to give 8.89 g of yellow oil (NMR CDCl$_3$ $^{31}$P: −1.59 ppm). The residue (8.89 g, 35.3 mmol) was dissolved in 35 ml of EtOH and to the solution was added Boc-anhydride (8 g, 36.6 mmol). The reaction mixture was stirred overnight at room temperature. The solvent was evaporated and residue was purified by column chromatography [eluent: EtOAc/2% MeOH] to yield 9.18 g (74%) as a white solid.

NMR (CDCl$_3$) H$^1$: 1.36 (t, J=5.4 Hz, 12H, 2×OCH(CH$_3$)$_2$), 1.43 (s, 9H, Boc), 3.29 (q, J=5.1 Hz, 2H, CH$_2$NH), 3.45 (q, J=5.4 Hz, 2H, CH$_2$NH), 4.78 (m, 2H, 2×OCH(CH$_3$)$_2$), 4.876 (s, 1H, NH), 7.47 (s,1H, NH).

b) 1-[4-phenoxybenzenesulfonamido]-2-[thisopropylphophonoformamido]ethane (Compound 1A)

The 1-Boc-amino-2-[diisopropylphosphonoformamido]ethane (0.97 g, 2.75 mmol) was dissolved in 5 ml TFA. Reaction was stirred for 0.5 hour and excess of TFA was removed in vacuo with toluene. To the residue in 15 ml DCM were added Et$_3$N (5 eq, 1.9 ml, 13.75 mmol) and 4-phenoxybenzenesulfonyl chloride (0.74 g, 2.75 mmol). The reaction was stirred overnight at room temperature. The mixture was washed with 1N HCl (3×25 ml) and the organic layer was dried over Na$_2$SO$_4$. The solvent was evaporated to give 0.97 g (70%) of a white solid, m.p.=99-106° C.

NMR (CDCl$_3$) $^{31}$P: −3.8 ppm, $^1$H: 1.35 (dd, J=5.7 Hz, 12H, 2×(CH$_3$)$_2$CHO), 2.0 (s, NH), 3.11 (q, J=5.4 Hz, 2H, NHCH$_2$), 3.46 (q, J=5.4 Hz, 2H, CH$_2$NH), 4.8 (m, J=6.6 Hz, 2H, 2×(CH$_3$)$_2$CHO), 7.04 (q, J=7.4 Hz, 4H), 7.2 (t, J=7.5 Hz, 1H), 7.4 (q, J=7.8 Hz, 2H), 7.65 (s, 1H, NH), 7.78 (d, J=6.9 Hz, 2H).

c) 1-[4-phenoxybenzenesulfonamido]-2-[phosphonoformamido]ethane (Compound 1, JS-268-1)

To the 1-[4-phenoxybenzenesulfonamido]-2-[diisopropylphophonoform amido]ethane (0.45 g, 0.93 mmol) in 10 ml CHCl$_3$ was added TMSBr (5 eq, 0.62 ml, 4.6 mmol) and reaction was stirred and heated at 50° C. for 2.5 hours. The reaction mixture was monitored by $^{31}$P NMR. The solvent was evaporated and to the mixture reaction was added 5 ml MeOH for one hour. The solvent was evaporated to give a yellow oil. The product was solidified from MeCN to give 0.29 g (78%) a white solid, m.p.=166-169° C.

NMR (D$_2$O) $^{31}$P: −3.12 ppm, $^1$H: 2.9 (t, J=6 Hz, 2H, NHCH$_2$), 3.18 (t, J=6.15 Hz, 2H, CH$_2$NH), 7.0 (d, J=8.7 Hz, 4H), 7.15 (t, J=7.3 Hz, 1H), 7.3 (t, J=8 Hz, 2H), 7.69 (d, J=6.6 Hz, 2H).

Compound 2: 1-[4-phenoxybenzenesulfonamido]-3-[phosphonoformamido]propane (JS-325-1), Scheme 2 a) 1-Boc-amino-3-[diisopropylphosphonoformamido]propane

To the solution of 3-(Boc-amino)propylamine (0.7 g, 4 mmol) in 10 ml CH$_3$CN was added PTF-P (1 eq, 1 g, 4 mmol). The reaction was stirred overnight at room temperature. The reaction mixture was monitored by $^{31}$P NMR. The solvent was evaporated to give yellow oil. The product was used in the next step without further purification.

b) 1-[4-phenoxybenzenesulfonamido]-3-[diisopropylphosphonoformamido]propane (Compound 2A)

1-Boc-amino-3-[diisopropylphosphonoformamido]propane (0.7 g, 4 mmol) was dissolved in 5 ml TFA. The reaction was stirred for 30 min. The excess of TFA was removed by evaporation in vacuo with toluene. To the residue in 15 ml DCM were added Et$_3$N (5 eq, 2.8 ml, 20 mmol) and 4-phenoxybenzenesulfonyl chloride (1 g, 45 mmol). The reaction was stirred overnight at room temperature. The mixture was washed with 1N HCl; the organic layer was dried over Na$_2$SO$_4$ and the solvent was evaporated. The product was purified by silica gel chromatography [eluent: CHCl$_3$/1-2% MeOH] to yield 1 g (50%) yellow oil.

NMR (CDCl$_3$) $^{31}$P: −3.48 ppm, $^1$H: 1.32 (dd, J=6.7 Hz, 12H, 2×(CH$_3$)$_2$CHO), 1.7 (m, J=6.3 Hz, 2H, CH$_2$), 2.9 (q, J=6.4 Hz, 2H, CH$_2$), 3.4 (q, J=6.3 Hz, 2H, CH$_2$), 4.7 (m, J=6.3 Hz, 2H, 2×(CH$_3$)$_2$CHO), 5.8 (t, J=6.6 Hz, NH), 7.04 (q, J=6 Hz, 4H), 7.2 (t, J=7.0 Hz, 1H), 7.4 (q, J=6.8 Hz, 2H), 7.6 (t, 1H, NH), 7.8 (d, J=6.7 Hz, 2H).

c) 1-[4-phenoxybenzenesulfonamido]-3-[phosphonoformamido]propane (Compound 2, JS-325-1)

To 1-phenoxybenzenesulfonamido-3-(diisopropylphosphonoformamido) propane (1 g, 2 mmol) in 15 ml $CHCl_3$ was added TMSBr (7 eq, 14 mmol, 1.9 ml) and the reaction was stirred with heating at 50° C. for 3 h. The reaction mixture was monitored by $^{31}P$ NMR. To the mixture reaction was added 5 ml MeOH for 1 h, after which the solvent was evaporated to give yellow oil. The product was solidified from MeCN to give 0.45 g (54%) white solid, m.p.=165-168° C.

NMR ($D_2O$) $^{31}P$: −3.0 ppm, $^1H$: 1.54 (m, J=6.9 Hz, 2H, $CH_2$), 2.8 (q, J=6.9 Hz, 2H, $CH_2$), 3.11 (q, J=6.9 Hz, 2H, $CH_2$), 7.02 (d, J=8.7 Hz, 4H), 7.18 (t, J=7.2 Hz, 1H), 7.35 (t, J=7.9 Hz, 2H), 7.7 (d, J=9 Hz, 2H). Anal. Calcd. for $C_{16}H_{19}O_7N_2PS$: C, 46.38; H, 4.62; N, 6.76. Found: C, 45.99; H, 4.54; N, 6.71.

Compound 3: 1-[4-phenoxybenzenesulfonamido]-4-[phosphonoformamido]butane (JS-343-1), Scheme 3 a) 1-[4-phenoxybenzenesulfonamido]-4-Boc-aminobutane

To the solution of 4-(Boc-amino)butylamine (0.54, 2.87 mmol) and $Et_3N$ (3 eq, 1.2 ml, 8.6 mmol) in 15 ml DCM was added 4-phenoxybenzenesulfonyl chloride solution (1 eq, 2.87 mmol, 0.77 g) in 10 ml DCM. The reaction was stirred overnight at room temperature. The reaction mixture was washed with 1N HCl, and the organic layer was dried over $Na_2SO_4$ and evaporated. The product was purified by silica gel chromatography [eluent: DCM/1-2% MeOH] to yield 0.32 g (27%) yellow oil.

NMR ($CDCl_3$) $^1H$: 1.42 (s, 9H, Boc), 1.49 (m, 4H, 2×$CH_2$), 2.95 (q, J=6.4 Hz, 2H, $CH_2$), 3.07 (q, J=5.0 Hz, 2H, $CH_2$), 4.56 (s, 1H, NH), 4.8 (s, 1H, NH), 7.05 (q, J=6 Hz, 4H), 7.2 (t, J=7.0 Hz, 1H), 7.4 (q, J=6.8 Hz, 2H), 7.6 (t, 1H, $CH_2$), 7.8 (d, J=6.7 Hz, 2H).

b) 1-[4-phenoxybenzenesulfonamido]-4-[diisopropylphophonoformamido]butane (Compound 3A)

1-[4-phenoxybenzenesulfonamido]-4-Boc-aminobutane (0.30 g, 0.72 mmol) was dissolved in 5 ml TFA. The reaction was stirred for 30 min and the excess of TFA was removed in vacuo with toluene. To the residue in 15 ml DCM were added $Et_3N$ (2 eq, 0.2 ml, 1.4 mmol) and PTF-P (1 eq, 0.18 g, 0.72 mmol) and stirred overnight at room temperature. The reaction mixture was monitored by $^{31}P$ NMR. The solvent was evaporated. The product was purified by silica gel chromatography [eluent: DCM/1-3% MeOH] to yield 0.14 g (38%) yellow oil.

NMR ($CDCl_3$) $^{31}P$: −3.24 ppm, $^1H$: 1.37 (dd, J=6.0 Hz, 12H, 2×($CH_3$)$_2$CHO), 1.58 (m, 4H, 2×$CH_2$), 2.9 (q, J=5.5 Hz, 2H, $CH_2$), 3.4 (q, J=5.5 Hz, 2H, $CH_2$), 4.79 (m, J=6.3 Hz, 2H, 2×($CH_3$)$_2$CHO), 4.9 (s,1H, NH), 7.05 (m, J=8.7 Hz, 4H), 7.2 (t, J=7.2 Hz, 1H), 7.4 (q, J=8.4 Hz, 2H), 7.6 (t, 1H, NH), 7.8 (dd, J =8.8 Hz, 2H).

c) 1-[4-phenoxybenzenesulfonamido]-4-[phosphonoformamido]butane (Compound 3, JS-343-1)

To 1-[4-phenoxybenzenesulfonamido]-4-[diisopropylphosphonoformamido] butane (0.14 g, 0.27 mmol) in 5 ml $CHCl_3$ was added TMSBr (5 eq, 1.9 ml, 14 mmol) and reaction was stirred and heated at 50° C. for 3 h. The reaction mixture was followed by $^{31}P$ NMR. To the mixture reaction was added 5 ml MeOH for 1 h and the solvent was evaporated to give yellow oil, which solidified in MeCN to give 0.11 g (96%) white solid, m.p.=143-145° C. m/z [M+H]$^+$ calcd/ found 429/429.4.

NMR ($D_2O$) $^{31}P$: −2.84 ppm, $^1H$: 1.3 (ws, 4H, 2×$CH_2$), 2.74 (t, 2H, J=6.5 Hz, $CH_2$), 3.01 (t, J=6 Hz, 2H, $CH_2$), 7.0 (d, J=8.7 Hz, 4H), 7.15 (t, J=7.2 Hz, 1H), 7.33 (t, J=7.8 Hz, 2H), 7.66 (d, J=9 Hz, 2H). Anal. Calcd. For $C_{17}H_{21}O_7N_2PS$: C, 47.66; H, 4.90; N, 6.54. Found: C, 47.3; H, 4.68; N, 6.45.

Compound 4: 1-Phenoxybenzenesulfonamido-5-[phosphonoformamido]pentane (JS-389-1), Scheme 4 a) 1-phenoxybenzenesulfonamido-5-(Boc-amino)pentane

To a solution of 5-(Boc-amino)pentylamine (12.8 mmol) and $Et_3N$ (2 eq, 3.55 ml, 25.6 mmol) in 30 ml $CH_3CN$ was added dropwise 4-phenoxybenzenesulfonyl chloride solution (1.1 eq, 3.44 g, 14 mmol) in 20 ml $CH_3CN$. The reaction was stirred overnight at room temperature. The precipitate was filtered and the solvent was evaporated. The product was purified by silica gel chromatography [eluent: $CH_2Cl_2$/1-2% MeOH] to yield 3.7 g (67%) pale yellow oil.

NMR ($CDCl_3$) $^1H$: 1.26-1.15 (m, 6H, 3×$CH_2$), 1.45 (s, 9H, Boc), 2.92 (t, J=6.6 Hz, 2H, $CH_2$), 3.05 (q, J=6.6 Hz, 2H, $CH_2$), 4.55 (s, 1H, NH), 4.81(t, 1H, NH), 7.05 (dd, J=8.7 Hz, 4H), 7.2 (t, J=7.5 Hz, 1H), 7.4 (t, J=8.1 Hz, 2H), 7.8 (d, J=9.0 Hz, 2H).

b) 1-(4-Phenoxybenzenesulfonamido)-5-(diethylphosphonoformamido)pentane (Compound 4A)

1-(4-Phenoxybenzenesulfonamido)-5-(Boc-amino)pentane (2.93 g, 0.25 mmol) was dissolved in 10 ml trifluoroacetic acid (TFA). The reaction was stirred for 30 min., the excess of TFA was removed in vacuo with toluene and the residue was taken up in 20 ml $CH_3CN$ containing $Et_3N$ (2 eq, 1.88 ml 13.5 mmol,) was treated dropwise by a solution of NPPF-E (purity 80%) (2 eq, 4.1 g, 13.5 mmol) in 20 ml of $CH_3CN$. After stirring the reaction mixture overnight at room temperature, the reaction mixture was monitored by $^{31}P$ NMR. The solvent was evaporated, the residue was diluted with $CH_2Cl_2$ and was washed successively by 0.5 N NaOH solution (4×50 ml), 1N HCl (3×50 ml) and finally by water (50 ml). The organic phase was dried over $Na_2SO_4$ and solvent was evaporated and the residue was purified by silica gel chromatography [eluent: $CH_2Cl_2$/1-5% MeOH] to yield 1.73 g (51%) a colorless oil.

NMR ($CDCl_3$) $^{31}P$: −1.19 ppm, $^1H$: 1.35-1.38 (m, 2H, $CH_2$), 1.37 (dd, J=6.0 Hz, 6H, 2×($CH_3CH_2O$)), 1.52 (m, 4H, 2$CH_2$), 2.92 (q, J=6.6 Hz, 2H, $CH_2$), 3.3 (q, J=6.7 Hz, 2H, $CH_2$), 4.78 (m, J=6.8 Hz, 4H, 2×($CH_3CH_2O$)), 4.88 (t, 1H, NH), 7.05 (t, J=8.0 Hz, 4H), 7.19 (t, 1H, NH), 7.2 (t, J=7.8 Hz, 1H), 7.4 (t, J=8.1 Hz, 2H), 7.8 (d, J=9.0 Hz, 2H).

c) 1-[4-Phenoxybenzenesulfonamido]-5-[phosphonoformamido]pentane (Compound 4, JS-389)

To 1-[4-phenoxybenzenesulfonamido]-5-[diethylphosphonoformamido]pentane (1.53 g, 3.07 mmol) in 20 ml $CHCl_3$ was added TMSBr (10 eq, 4.05 ml, 30 mmol) and reaction was stirred and heated at 50° C. for 3 h. The reaction mixture was followed by $^{31}P$ NMR. The solvent was evaporated and to the residue was added MeOH (20 ml) for half hour. Evaporation of the solvent gave a pale yellow solid. The solid was washed with $CH_3CN$ to give 1.1 g (81%) white solid, m.p.=153-155° C.

NMR ($D_2O$+$NaHCO_3$) $^{31}P$: −1.32. ppm, $^1H$: 1.1 (m, J=7.5 Hz, 2H, $CH_2$), 1.27 (m, 4H, 2×$CH_2$), 2.7 (t, J=7.0 Hz, 2H, $CH_2$), 2.97 (t, J=6.9 Hz, 2H, $CH_2$), 6.98 (d, J=8.0 Hz, 4H), 7.14 (t, J=7.4 Hz, 1H), 7.3 (t, J=7.8 Hz, 2H), 7.65 (d, J=8.4 Hz, 2H). Anal. Calcd. For $C_{18}H_{23}O_7N_2PS$: C, 48.86; H, 5.2; N, 6.33. Found: C, 48.79; H, 5.13; N, 6.28. m/z [M+H]$^+$ calcd/found 443/443.

Compound 5: 1-[4-Phenoxybenzenesulfonamido]-6-[phosphonoformamido]hexane (JS-403), Scheme 5 a) 1-[4-phenoxybenzenesulfonamido]-6-(Boc-amino)hexane

To a solution of 6-(Boc-amino)hexylamine (4.95 g, 23 mmol) and $Et_3N$ (2 eq, 6.4 ml, 46 mmol) in 25 ml $CH_3CN$ was added dropwise 4-phenoxybenzenesulfonyl chloride solution (1 eq, 6.16 g, 23 mmol) in 15 ml $CH_3CN$. The reaction was stirred for 2 days at room temperature. The precipitate was filtered and the solvent was evaporated. The residue was purified by silica gel chromatography [eluent: $CH_2Cl_2$/1-2% MeOH] to yield 6.68 g (64%) a colorless oil, which solidified to a white solid, m.p.=77-78° C.

NMR ($CDCl_3$) $^1H$: 1.12 (s, 2H, $CH_2$), 1.406-1.43 (m, 6H, 3×$CH_2$), 1.4 (s, 9H, Boc), 2.94 (q, J=6.9 Hz, 2H, $CH_2$), 3.08 (q, J=6.3 Hz, 2H, $CH_2$), 4.53 (s, 1H, NH), 7.06 (dd, J=7.3 Hz, 4H), 7.24 (t, J=6.3 Hz, 1H), 7.4 (t, J=6.6 Hz, 2H), 7.8 (d, J=6.9 Hz, 2H). Anal. Calcd. For $C_{23}H_{32}O_5N_2S$: C, 61.58; H, 7.19; N, 6.24. Found: C, 61.28; H, 7.19; N, 6.24.

b) 1-[4-Phenoxybenzenesulfonamido]-6-[diethylphosphonoformamido]hexane (Compound 5A)

1-[4-Phenoxybenzenesulfonamido]-6-(Boc-amino)hexane (6.68 g, 14.9 mmol) was dissolved in 25 ml TFA. The reaction was stirred for 30 min and the excess TFA was removed in vacuo with toluene. To the residue dissolved in 40 ml $CH_3CN$ containing $Et_3N$ (2 eq, 4.14 ml, 29.8 mmol) was added dropwise NPPF-E (purity 80%) (2 eq, 9 g, 29.8 mmol) dissolved in 30 ml $CH_3CN$. The reaction was stirred overnight at room temperature after which the reaction mixture was monitored by $^{31}P$ NMR. The solvent was evaporated; the residue was diluted with $CH_2Cl_2$ and was washed successively by 0.5N NaOH (4×50 ml) and 1N HCl (3×50 ml), then by water (50 ml). The organic phase was dried over $Na_2SO_4$ and solvent was evaporated and the residue was purified by silica gel chromatography [eluent: $CH_2Cl_2$/1-5% MeOH] to yield 5 g (75%) of a colorless oil.

NMR ($CDCl_3$) $^{31}P$: −1.1 ppm, $^1H$: 1.28-1.35 (m, 4H, 4×$CH_2$), 1.35 (dd, J=7.2 Hz, 6H, 2×($CH_3CH_2O$)), 1.423-1.55 (m, 4H, 2×$CH_2$), 2.9 (q, J=6.3 Hz, 2H, $CH_2$), 3.29 (q, J=6.6 Hz, 2H, $CH_2$), 4.22 (m, J=6.8 Hz, 4H, 2×($CH_3CH_2O$)), 5.08 (s, 1H, NH), 7.06 (dd, J=7.3 Hz, 4H), 7.24 (t, J=6.3 Hz, 1H), 7.4 (t, J=6.6 Hz, 2H), 7.8 (d, J=6.9 Hz, 2H).

c) 1-[4-Phenoxybenzenesulfonamido]-6-[phosphonoformamido]hexane (Compound 5, JS-403)

To 1-[4-phenoxybenzenesulfonamido]-6-(diethylphosphonoformamido) hexane (4.66 g, 9.1 mmol) in 2 ml $CHCl_3$ was added TMSBr (7 eq, 8.4 ml, 63.7 mmol) and reaction was refluxed for 2.5 h. The reaction mixture was monitored by $^{31}P$ NMR. The solvent was evaporated and to residue was added MeOH (20 ml) for hour. The solvent was evaporated to a yellow oil, which was solidified to give 3.98 g (98%) as a pale brown solid, m.p.=117-120° C.

NMR ($D_2O$+$NaHCO_3$) $^{31}P$: −1.04 ppm, $^1H$: 0.98 (ws, 4H, 2×$CH_2$), 1.13-1.26 (dt, J=6.6 Hz, 4H,2×$CH_2$), 2.53 (t, J=7.0 Hz, 2H, $CH_2$), 2.95 (t, J=6.7 Hz, 2H, $CH_2$), 6.62 (dd, J=6.6 Hz, 4H), 6.82 (t, J=7.3 Hz, 1 H), 6.98 (t, J=7.8 Hz, 2H), 7.48 (d, J=8.6 Hz, 2H). Anal. Calcd. For $C_{19}H_{25}O_7N_2S$: C, 50.0; H, 5.52; N, 6.14. Found: C, 49.63; H, 5.56; N, 6.21.

Compound 8: 2-amino-1-(4-phenoxybenzenesulfonamido)-3-[phosphonoformamido]propane (JS-489-1), Scheme 6 a) N,N'-di-Boc-2-hydroxy-1,3-diaminopropane

To a solution of 2-hydroxy-1,3-diaminopropane (5.1 g, 56.6 mmol) in 25 ml water was added $Boc_2O$ (24.6 g, 113 mmol) in 50 ml dioxane followed by $Na_2CO_3$ (13.76 g, 141 mmol) at 0° C. and stirring for 2 h. The reaction mixture was allowed to warm to room temperature and was then stirred for an additional 16 h. Then the solvents were evaporated, the residue was diluted with water and extracted with EtOAc (3×50 ml). The organic phase was dried over $Na_2SO_4$ and the solvent was evaporated. Recrystallisation of product from hot cyclohexane gave 13.19 g (80%) white solid. M.p.=92° C.

NMR ($CDCl_3$) $^1H$: 1.46 (s, 18H, Boc), 3.1-3.32 (m, 4H, 2×$CH_2$), 3.73 (m, 1H, CH), 5.11 (bs, NH).

b) N,N'-di-Boc-2-methanesulfonyloxy-1,3-diaminopropane

To a solution of N,N'-di-Boc-2-hydroxy-1,3-diaminopropane (13.19 g, 45.4 mmol) and triethylamine (1.5 eq, 9.5 ml, 68.1 mmol) in dry 50 ml $CH_2Cl_2$ was added dropwise a solution of methanesulfonyl chloride (1.5 eq, 5.25 ml, 68 mmol) in dry 15 ml $CH_2Cl_2$ over a period of 1 h at 0° C. with stirring under nitrogen. After the addition, the reaction was stirred overnight at room temperature. Water was slowly added to quench the reaction; the organic layer was separated and then washed with water (5×15 ml) and dried over $Na_2SO_4$ and evaporated to give white solid. Recrystallization from hot acetone and cyclohexane gave 10.36 g (62%) white solid. M.p.=127° C.

NMR ($CDCl_3$) $^1H$: 1.43 (s, 18H, Boc), 3.1 (s, 3H, $CH_3$), 3.26-3.34 (m, 2H, $CH_2$), 3.45-3.54 (m, 2H, $CH_2$), 4.66 (m, 1H, CH), 5.2 (bs, NH).

c) 2-azido-$N^1$,$N^3$-bis-Boc-1,3-diaminopropane

To a solution of the N,N'-bis-Boc-2-methansulfonyl-1,3-diaminopropane (10.36 g, 28 mmol) in 60 ml dry DMF was added sodium azide (4 eq, 7.3 g, 112 mmol), and the mixture was refluxed for 12 h at 70° C. The reaction mixture was cooled and poured into water. The solid, which formed, was filtered and washed with water to give 9.45 g (94%) of product. M.p.=75-77° C.

NMR ($CDCl_3$) $^1H$: 1.44 (s, 18H, Boc), 3.10-3.17 (m, 2H, $CH_2$), 3.3-3.6 (m, 2H, $CH_2$), 3.64 (m, 1H, CH), 4.72 (bs, NH), 5.08 (bs, NH). IR (NaCl): 2115 cm$^{-1}$($N_3$).

d) 2-azido-3-[diethylphosphonoformamido]propylamine

2-Azido-$N^1$,$N^3$-di-Boc-1,3-diaminopropane (3.34 g, 10.6 mmol) was dissolved in 10 ml TFA. The reaction was stirred for 30 min and the excess of TFA was removed in vacuo with toluene. To the residue in 25 ml of $CH_3CN$ with DIEA (2.2 eq, 3.86 g, 12.7 mmol) and DMAP (0.13 g, 10% mol) was added very slowly NPPF-E solution (1.2 eq, 3.86 g, 12.7 mmol) in 15 ml $CH_3CN$. The reaction was stirred overnight at room temperature. The reaction mixture was followed by $^{31}P$ NMR. The white precipitate which formed was collected by filtration and washed with $CH_3CN$ to give 1.26 g (43%) solid. M.p.=154-156° C.

NMR (DMSO-d) $^{31}P$: −0.75; $^1H$: 1.28 (dd, J=7.2 Hz, 6H, 2×$CH_3CH_2O$), 2.69-2.77 (m, 1H, $CH_2$), 2.99-3.04 (m, 1H, $CH_2$), 3.4 (m, J=7.1 Hz, 2H, $CH_2$), 4.01 (m, 1H, CH), 4.14 (m, 4H, 2×$CH_3CH_2O$).

e) 2-Azido-1-(4-phenoxybenzenesulfonamido)-3-[diethylphosphonoformamido]propane (Compound 9)

To a solution of 2-azido-3-[diethylphosphonoformamido]propylamine (1.26 g, 4.5 mmol) and triethylamine (1.2 eq, 1.46 g, 5.4 mmol) in 15 ml $CH_3CN$ was added dropwise 4-phenoxybenzenesulfonyl chloride solution (1.5 eq, 68 mmol, 5.25 ml) in 15 ml $CH_3CN$ at 0° C. with stirring. After the addition, the reaction was stirred overnight at room temperature. The solvent was evaporated and the residue was purified by silica gel chromatography [eluent: DCM/1% MeOH] to yield 1.36 g (60%) a pale yellow oil.

NMR ($CDCl_3$) $^{31}P$: −2.18; $^1H$: 1.35 (dd, J=7.2 Hz, 6H, 2×$CH_3CH_2O$), 2.91-3.08 (m, 2H, $CH_2$), 3.41-3.48 (m, 1H, $CH_2$), 3.57-3.6 (m, 1H, $CH_2$), 3.8 (m, J=5.7 Hz, 1H, CH), 4.22 (m, 4H, 2×$CH_3CH_2O$), 5.75 (t, 1H, NH), 7.05 (dd, J=8.5 Hz, 4H), 7.22 (t, J=7.6 Hz, 1H), 7.4 (t, J=7.9 Hz, 2H), 7.8 (d, J=8.7 Hz, 2H).

2-Boc-amino-1-(4-phenoxybenzenesulfonamido)-3-[diethylphosphonoformamido]propane (Compound 8A)

To a stirred solution of 2-azido-1-phenoxybenzenesulfonamido-3-[diethylphosphonoformamido]propane (0.36 g, 0.7 mmol) in a mixture of pyridine and $NH_4OH$ (7:1, 5 ml) was added $PMe_3$ (1M in THF) (3 eq, 2.1 mmol, 2.1 ml) and the reaction mixture was stirred under nitrogen for 3 h. The solution was diluted with EtOH (5 ml) and water (1 ml) and concentrated. The resulting residue was dissolved in a mixture of toluene and EtOH (1:1, 16 ml) and concentrated again to yield 0.36 g of yellow oil. The absence of azide group was verified by IR. The product was dissolved in 10 ml of pyridine and to the solution was added slowly Boc-anhydride at 0° C. The reaction was stirred 3 days at room temperature. The reaction mixture was followed by $^{31}P$ NMR. Two major peaks were observed at −0.5 and −0.8 ppm. The reaction was stopped and solvent was evaporated. The residue was dissolved in 15 ml EtOAc and washed with 0.5N HCl (2×5 ml), $NaHCO_3$ (2×5 ml) and water (5 ml). The organic phase was collected and dried over $Na_2SO_4$. The residue was purified by silica gel column chromatography [eluent: EtOAc/Petr. Ether (3:7)] to yield 60 mg (15%) a colorless oil.

NMR ($CDCl_3$) $^{31}P$: −1.88; $^1H$: 1.35 (dd, J=6.8 Hz, 6H, 2×$CH_3CH_2O$), 1.42 (s, 9H, Boc), 2.98 (s, 2H, $CH_2$), 3.49 (s, 2H, $CH_2$), 3.76 (s,1H, CH), 4.22 (m, 4H, 2×$CH_3CH_2O$), 5.45 (s, 1H, NH), 6.12 (s, 1H, NH), 7.05 (dd, J=8.2 Hz, 4H), 7.23 (t, J=7.5 Hz, 1H), 7.4 (t, J=7.7 Hz, 2H), 7.8 (d, J=8.5 Hz, 2H), 8.02 (s, 1H, NH), g) 1-(4-phenoxybenzenesulfonamido)-2-amino-3-[phosphonoformamido]propane (Compound 8, JS-489-1)

2-Boc-amino-1-phenoxybenzenesulfonamido-3-[diethylphosphonoformamido]propane (50 mg, 0.085 mmol) was dissolved in 2 ml TFA. The reaction was stirred for 30 min and the excess of TFA was removed in vacuo with toluene. The residue was dissolved in 2 ml $CHCl_3$ and to solution was added TMSBr (10 eq, 0.12 ml, 0.85 mmol) and reaction was stirred and heated at 50° C. for 3 h. The reaction mixture was followed by $^{31}P$ NMR. The solvent was evaporated and to the residue was added MeOH (2 ml) for half hour. The solvent was evaporated to give brown foam, which solidified from EtOH. The white solid was filtered and washed with $CH_3CN$ to give 4 mg of product.

NMR ($D_2O$+$NaHCO_3$) $^{31}P$: −1.096; $^1H$: 2.81-2.96 (m, 2H, $CH_2$), 3.13-3.28 (m, 2H, $CH_2$), 3.58 (m, 1H, CH), 7.08 (dd, J=9.0 Hz, 4H), 7.2 (t, J=7.5 Hz, 1H), 7.4 (t, J=8.0 Hz, 2H), 7.58 (d, J=9.0 Hz, 2H).

Compound 10: N-{2-[2-(4-Phenoxybenzenesulfonylamino)-ethylamino]-ethyl}-carbamoylphosphonic acid (JS-426), Scheme 7 a) (2-Aminoethyl)-(2-tert-butoxycarbonylaminoethyl)-carbamic acid tert-butyl ester To the solution of diethylenetriamine (1.88 g, 13 mmol) in 15 ml $CH_2Cl_2$ was added dropwise ethyl trifluoroacetate (1.365 g, 13 mmol) in 15 ml of same solvent, while keeping the temperature at 0° C. After complete addition, the mixture was stirred for 2 hours at 0° C. and then for 2 hours at room temperature. The solvent was evaporated to give yellow oil which was used without further purification. This compound was dissolved in 25 ml $CH_2Cl_2$ and Boc-anhydride (26 mmol, 5.67 g) was added dropwise to the solution under cooling to −10° C. After complete addition, the reaction was stirred for 24 h at room temperature. The solvent was evaporated to give dense yellow oil, which was dissolved in a mixture of methanol (280 ml) and distilled water (20 ml).

To the mixture was added $K_2CO_3$ and the reaction was refluxed for 2 h. After filtration, the solvent was evaporated the residue was redissolved in water and pH adjusted to pH=13 with 40% NaOH. The product was extracted with $CH_2Cl_2$ and collected organic phase was dried over $Na_2SO_4$. The solvent was evaporated to give 2.42 g (61%) yellow oil.

NMR ($CDCl_3$) $^1H$: 1.42-1.46 (ds, 18H, Boc), 1.42-1.46 (ds, 2H, $CH_2$), 3.3 (m, 6H, 3×$CH_2$).

b) (2-Diethylphosphonoformamidoethyl)-(2-tert-butoxycarbonylaminoethyl)-carbamic acid tert-butyl ester To the solution of the bis-Boc derivative obtained in the previous step (1.42 g, 4.68 mmol) in 15 ml $CH_3CN$ was added DIEA (2 eq, 0.81 ml) and then was added dropwise NPPF-E (4.68 mmol, 1.4 g) dissolved in 15 ml $CH_3CN$. The reaction was stirred for overnight at room temperature after which the examination of the reaction mixture by $^{31}P$ NMR showed that the reaction was finished. The reaction was stirred overnight at room temperature. The examination of reaction mixture by $^{31}P$ NMR indicated the end of the reaction. The solvent was evaporated. The residue was diluted with $CH_2Cl_2$ and was washed by 0.5N NaOH (4×50 ml) and 1N HCl (3×50 ml), then by water (50 ml). The organic phase was dried over $Na_2SO_4$ and solvent was evaporated to give 1.7 g (77%) yellow oil. The slightly impure product was used in the next step without further purification.

NMR ($CDCl_3$) $^{31}P$: −1.61 ppm, $^1H$: 1.31 (dd, J=7.2 Hz, 6H, 2×($CH_3CH_2O$)), 1.4-1.44 (ds, 18H, Boc), 3.22-3.44 (m, 8H, $CH_2$), 4.2 (m, 4H, 2×($CH_3CH_2O$)).

c) Diethyl N-{2-[2-(4-Phenoxybenzenesulfony-lamino)-ethylamino]-ethyl}carbamoyl phosphonate (Compound 10A)

N-(2-Diethylphosphonoformamidoethyl)-N-(2-tert-butoxycarbonylamino ethyl)-carbamic acid tert-butyl ester obtained in the previous step (1.7 g, 3.6 mmol) was dissolved in 10 ml TFA. The reaction was stirred for 30 min and the excess of TFA was removed in vacuo with toluene. To the residue in 25 ml of 70% 2-propanol was added DIEA (3 eq, 10.8 mmol, 1.88 ml) and then, was added slowly 4-phenoxybenzenesulfonyl chloride (3.6 mmol, 0.966 g). The reaction was stirred overnight at room temperature. The reaction mixture was followed by $^{31}$P NMR. The product was extracted with $CH_2Cl_2$ and the organic phase was collected and dried over $Na_2SO_4$. The residue was purified by silica gel column chromatography [eluent: $CHCl_3$/5% MeOH] to yield 0.8 g a pale yellow oil. The product was found to contain excess of diisopropylethylamine salt, yet it was used in the next step without further purification.

NMR ($CDCl_3$) $^{31}$P: −2.65 ppm. m/z [M+H]$^+$ calcd/found 500.5/500.27.

d) N-{2-[2-(4-Phenoxy-benzenesulfonylamino)ethylamino]-ethyl}carbamoyl-phosphonic acid (Compound 10, JS-415)

To the diethyl N-{2-[2-(4-phenoxy-benzenesulfonylamino)-ethylamino]-ethyl}-carbamoylphosphonate obtained in the previous step (0.61 g, 1.22 mmol) in 10 ml $CHCl_3$ was added TMSBr (10 eq, 1.61 ml, 12 mmol) and reaction was stirred and heated at 50° C. for 3 h. The reaction mixture was followed by $^{31}$P NMR. The solvent was evaporated and to the residue was added MeOH (20 ml) for half hour. The solvent was evaporated to give yellow oil, which was solidified from water to give 40 mg white solid, m.p.=224-225° C. The most amount of the product was not solidified.

NMR ($D_2O$+$NaHCO_3$+NaOH) $^{31}$P: −1.41 ppm, $^1$H: 2.53 (q, J=7 Hz, 2H, $CH_2$), 2.83 (q, J=6.3 Hz, 2H, $CH_2$), 3.02-3.15 (m, 4H, 2×$CH_2$) 7.0 (d, J=8.1 Hz, 4H), 7.12 (t, J=7.2 Hz, 1H), 7.3 (t, J=7.5 Hz, 2H), 7.78 (d, J=8.7 Hz, 2H). m/z [M+H]$^+$ calcd/found 444.5/444.6.

Compound 8S: (S)-N-[2-amino-3-(4-phenoxybenzenesulfonamido)propyl]carbamoylphosphonic acid, Scheme 8 a. (S)-3-diisopropylphosphonoformamido-2-(tritylamino)propanol, Scheme 8A

A solution of diisopropyl 4-nitrophenoxycarbonylphosphonate (i-Pr-NPPF) (9.27 g, 28 mmol) in dry $CH_2Cl_2$ (50 mL) was added dropwise to a solution of (S)-2-triphenylmethylamino-3-aminopropanol (9.3 g, 28 mmol) in dry $CH_2Cl_2$ (100 mL) at 0° C. The reaction mixture was stirred at room temperature for 1 h. Workup was done by washing the reaction mixture successively with 0.5 M NaOH and water. The organic layer was dried over anhydrous $Na_2SO_4$ and concentrated. The residue obtained was purified by column chromatography (silica gel, 70% EtOAc in pet. ether) to provide (S)-3-diisopropylphosphonoformamido-2-(tritylamino)propanol as gummy solid in 82% (12.0 g) yield.

IR (Neat):ν 3396, 3320, 2977, 2939, 1649 cm$^{-1}$; NMR [$CDCl_3$,$D_2O$ (two drops)] $^{31}$P: δ −3.43 ppm. $^1$H: δ 1.24-1.42 (m, 12H), 2.40-2.55 (m, 1H), 2.64-2.80 (m, 1H), 2.92-3.32 (m, 3H), 4.60-4.90 (m, 2H), 7.08-7.38 (m, 9H), 7.45-7.59 (m, 6H); MS-ES (m/z): 243, 283 (M$^{+1}$).

b. (S)-2-benzyloxycarbonylamino 3-(diisopropylphosphonoformamido)propanol, Scheme 8B (S)-3-diisopropylphosphonoformamido-2-(tritylamino) propanol (10.49 g, 20 mmol) was dissolved in a mixture of chloroform-methanol (1:1, 40 mL) and cooled to 0° C. in an ice bath. The reaction mixture was stirred at RT for 7 h, after dropwise addition of trifluoroacetic acid (20.0 mmol, 1.5 mL) at 0° C. The solvents were removed and the resulting residue was azeotroped 5 times with diethyl ether (5×40 mL) and partitioned between diethyl ether (150 mL) and water (50 mL). The ether layer was washed with water (20 mL) and the combined aqueous fractions were basified with $NaHCO_3$ (80 mmol, 6.72 g). Aqueous fraction was diluted with EtOAc (150 mL) and the mixture was cooled to 0° C. in an ice bath. Benzyl chloroformate (2.9 mL, 20 mmol) was then added to the reaction mixture at 0° C. and stirred vigorously at RT for 1.5 h. The layers were separated and the aqueous layer was washed with EtOAc (2×30 mL). The combined organic fractions were washed with brine (40 mL), dried over anhydrous $Na_2SO_4$ and concentrated. The residue was purified by column chromatography (silica gel, 5% MeOH in EtOAc) to afford (S)-2-benzyloxycarbonylamino 3-(diisopropylphosphonoformamido)propanol as gummy solid in 50% (4.16 g) yield.

IR (Neat): ν 3313, 2977, 2939, 1713, 1649 cm$^{-1}$; NMR ($CDCl_3$) $^{31}$P:δ −3.82 ppm. $^1$H: δ 1.28-1.37 (m, 12H), 3.44-3.56 (m, 3H), 3.56-3.70 (m, 2H), 3.72-3.86 (m, 1H), 4.66-4.84 (m, 2H), 5.03-5.14 (m, 2H), 5.66-5.74 (m, 1H), 7.30-7.36 (m, 5H), 7.96-8.06 (m, 1H); MS-ES (m/z): 417 (M$^{+1}$).

c. Diisopropyl N-[2-benzyloxycarbonylamino-3-(-N-tert-butoxycarbonyl)-3-(-4-phenoxybenzenesulfonamido)propyl]carbamoylphosphonate, Scheme 8C To a solution of (S)-2-benzyloxycarbonylamino 3-(diisopropylphosphonoformamido)propanol (0.208 g, 0.5 mmol) in toluene (5 mL) was added $PPh_3$ (0.144 g, 0.55 mmol) and the mixture was stirred for 5 min. To this solution, N-(tert-butoxy) N-(4-phenoxybenzenesulfonyl) carbamate (0.192 g, 0.55 mmol) was added followed by the slow addition of DEAD (0.09 mL, 0.55 mmol). The reaction was stirred at RT for 12 h. The reaction mixture was filtered, solvent was evaporated and the residue obtained was purified through column chromatography (silica gel, 30% EtOAc in n-hexane) to provide the product as colorless solid solid in 38% (0.140 g) yield.

IR (Neat): ν 3298, 2973, 1647 cm$^{-1}$; NMR ($CDCl_3$) $^{31}$P: δ −3.56 ppm. $^1$H: δ 1.25-1.32 (m, 21 H), 3.33-3.65 (m, 2H), 3.75-3.95 (m, 2H), 4.05-4.25 (m, 1H), 4.65-4.85 (m, 2H), 4.95-5.15 (m, 2H), 5.49 (d, 1H, J=7.2 Hz), 6.90 (dd, 2H, J=9.0, 1.2 Hz), 6.95-6.02 (m, 2H), 7.13-7.20 (m, 2H), 7.20-7.28 (m, 4H), 7.30-7.38 (m, 2H), 7.48-7.58 (m, 1H), 7.73 (d, 2H, J=7.8 Hz); MS-ES (m/z): 748 (M$^{+1}$).

d. Diisopropyl (S)-2-benzyloxycarbonylamino-3-(4-phenoxybenzenesulfonamido)-propylcarbamoylphosphonate, Scheme 8D To a stirred solution of diisopropyl N-[2-benzyloxycarbonylamino-3-(-N-tert-butoxycarbonyl)-3-(-4-phenoxybenzenesulfonamido)propyl]carbamoylphosphonate (0.28 g, 0.37 mmol) in $CH_2Cl_2$ (1.5 mL), was added dropwise trifluoroacetic acid (1.5 mL). The reaction mixture was stirred at RT for 2 h, quenched with saturated NaHCO$_3$ solution, extracted with EtOAc (3×20 mL) and finally washed with brine. Combined organic layers were dried over anhydrous Na$_2$SO$_4$, concentrated and column purified (silica gel, 70% EtOAc in n-hexane) to provide diisopropyl (S)-2-benzyloxycarbonylamino-3-(4-phenoxybenzenesulfonamido) propylcarbamoyl phosphonate as colorless solid in 90% (0.217 g) yield.

NMR (CDCl$_3$) $^{31}$P: δ −4.06 ppm. $^1$H: δ 1.15-1.35 (m, 12H), 2.85-3.05 (m, 2H), 3.30-3.58 (m, 2H), 3.60-3.80 (m, 1H), 4.60-4.76 (m, 2H), 4.99 (s, 2H), 5.74 (d, 1H, J=7.4 Hz), 5.83 (t, 1H, J=6.6 Hz), 6.90-7.02 (m, 4H), 7.12-7.21 (m, 2H), 7.22-7.29 (m, 4H), 7.30-7.38 (m, 2H), 7.59-7.67 (m, 1H), 7.70 (d, 2H, J=9.0 Hz); MS-ES (m/z): 648.0 (M$^{+1}$).

e. (S)-N-[2-Amino-3-(4-phenoxybenzenesulfonamido)propyl]carbamoylphosphonic acid, Scheme 8E To a stirred solution of diisopropyl (S)-2-benzyloxycarbonylamino-3-(4-phenoxybe-nzenesulfonamido)propylcarbamoylphosphonate (0.10 g, 0.15 mmol, 1 equivalents) in CHCl$_3$ (2 mL), was added TMSBr (0.20 mL, 1.5 mmol, 10 equivalents) dropwise. The reaction mixture was stirred for 12 h at 50° C. Then two 5 equivalents of TMSBr was added to the reaction mixture in an interval of 24 h. After completion of the reaction ($^{31}$P NMR −20.5 ppm), solvent was evaporated. Methanol was added to the reaction mixture and stirred at RT for 1 h. Solvents were evaporated and the product was solidified using MeOH. Mother liquor was evaporated and the product was solidified from residue using EtOH, to obtain a second crop of the product as white solid in 47% [0.031 g (includes first crop product)].

Mp: 220-235° C.; NMR (D$_2$O+NaHCO$_3$) $^{31}$P: δ −0.89 ppm. $^1$H: δ 2.65-2.98 (m, 2H), 3.00-3.28 (m, 2H), 3.42-3.60 (m, 1H), 6.96-7.22 (m, 5H), 7.23-7.42 (m, 2H), 7.69 (d, 2H, J=9.0 Hz); MS-ES (m/z): 430 (M$^{+1}$).

Compound 8R: (R)-N-[2-amino-3-(4-phenoxybenzenesulfonamido)propyl]carbamoylphosphonic acid, Scheme 9 a. (S)-3-(4-phenoxybenzenesulfonamido)-2-(tritylamino)propanel, Scheme 9A

To a solution of (S)-2-triphenylmethylamino-3-aminopropanol (1.99 g, 6 mmol) in CH$_2$Cl$_2$ (12 mL) at 0° C., triethylamine (1.7 mL, 12 mmol) was added dropwise followed by the addition of 4-phenoxybenzenesulfonyl chloride (1.61 g in 12 mL CH$_2$Cl$_2$). The reaction mixture was stirred at RT for 2 h and then was washed with water (20 mL) and brine (20 mL). The organic layer was dried over anhydrous Na$_2$SO$_4$, concentrated and purified through column chromatography (silica gel, 35% EtoAc in pet. ether) to afford (S)-3-(4-phenoxybenzenesulfonamido)-2-(tritylamino)propanol as colorless solid in 74% (2.52 g) yield.

Mp: 67-70° C.; IR (Neat): ν 3302, 3059, 3019 cm$^{-1}$; $^1$H NMR (CDCl$_3$): δ 2.10 (bs, 1H), 2.37-2.49 (m, 1H), 2.6-2.7 (m, 1H), 2.76-2.87 (m, 2H), 3.13-3.23 (m, 1H), 4.67-4.84 (m, 1H), 6.90-6.96 (m, 2H), 6.97-7.03 (m, 2H), 7.07-7.23 (m, 10H), 7.31-7.44 (m, 9H), 7.61 (d, 2H, J=9.0 Hz); MS-ES (m/z): 243, 323 (M$^{+1}$).

b. (S)-2-(benzyloxycarbonylamino)-3-(4-phenoxybenzenesulfonamido)propanol, Scheme 9B (S)-3-(4-phenoxybenzenesulfonamido)-2-(tritylamino)propanol (2.26 g, 4.0 mmol) was dissolved in a mixture of chloroform and methanol (1:1, 8 mL) and cooled to 0° C. in an ice bath. The reaction mixture was stirred at 0° C. for 2.5 h, after dropwise addition of trifluoroacetic acid (5.2 mL, 70 mmol). Solvents were removed and the resulting residue was azeotroped 5 times with diethyl ether (5×2 mL) and partitioned between diethyl ether (50 mL) and water (25 mL). The ether layer was washed with water (10 mL) and the combined aqueous fractions are basified with NaHCO$_3$ (1.34 g, 16 mmol). Aqueous fraction was diluted with EtOAc (100 mL) and the mixture was cooled to 0° C. in an ice bath. Then benzyl chloroformate (0.57 mL, 4.0 mmol) was added to the reaction mixture and stirred vigorously at RT for 1.5 h. The layers were separated and the aqueous layer was washed with EtOAc (2×20 mL). The combined organic fractions were washed with brine (20 mL), dried over anhydrous Na$_2$SO$_4$, concentrated and column purified (silica gel, 5% MeOH in EtOAc) to provide (S)-2-(benzyloxycarbonyla-mino)-3-(4-phenoxybenzenesulfonamido) propanol in 76% (1.38 g, 4.0 mmol) yield as colorless solid.

Mp: 86-89° C.; IR (Neat): ν 3368, 3295, 3059, 1704 cm$^{-1}$; NMR (CDCl$_3$): $^1$H: δ 2.66-2.75 (m, 1H), 3.04-3.2 (m, 2H), 3.60-3.92 (m, 3H), 5.05 (s, 2H), 5.44-5.53 (m, 2H), 6.96-7.10 (m, 4H), 7.19-7.27 (m, 1H), 7.29-7.36 (m, 5H), 7.37-7.46 (m, 2H), 7.75 (d, 2H, J=9.0 Hz).

c. (R)-2-(benzyloxycarbonylamino)-3-(4-phenoxybenzenesulfonamido)propyl azide, Scheme 9C To a solution of (S)-2-(benzyloxycarbonylamino)-3-(4-phenoxybenzene sulfonamido) propanol (0.45 g, 1.0 mmol) in toluene (10 mL) was added PPh$_3$ (0.28 g, 1.1 mmol) and the mixture was stirred at RT for 5 min. After adding hydrazoic acid (1.25 M in toluene, 1.04 mL, 1.3 mmol), DEAD (0.17 mL, 1.1 mmol) was added dropwise. The reaction mixture was stirred at RT for 30 min, filtered and solvent was evaporated. The crude residue was chromatographed (silica gel, 30% EtOAc in n-hexane) to afford (R)-2-(benzyloxycarbonylamino)-3-(4-phenoxybenzenesulfon amido) propyl azide as white solid in 60% (0.29 g) yield.

IR (Neat): ν 3296, 2101, 1699 cm$^{-1}$; NMR (CDCl$_3$) $^1$H: δ 2.85-3.10 (m, 2H), 3.35-3.55 (m, 2H), 3.70-3.85 (m, 1H), 5.01 (s, 2H), 5.10 (t, 1H, J=6.0 Hz), 5.22 (d, 1H, J=9.0 Hz), 6.90-7.03 (m, 4H), 7.12-7.20 (m, 2H), 7.23-7.30 (m, 4H), 7.31-7.38 (m, 2H), 7.69 (d, 2H, J=9.0 Hz).

d. Diisopropyl (R)-N-[2-(benzyloxycarbonylamino)-3-(4-phenoxybenzenesulfonamido)propyl]carbamoylphosphonate, Scheme 9D Trimethylphosphine (0.93 mL, 0.933 mmol, 1 M solution) was added dropwise to a stirred solution of (R)-2-(benzyloxycarbonylamino)-3-(4-phenoxybenzenesulfonam-ido)propyl azide (0.15 g, 0.31 mmol) in dry CH$_2$Cl$_2$ (1.0 mL). The reaction mixture was stirred at RT for 1.5 h under nitrogen atmosphere. iPr-NPPF (0.15 g, 0.46 mmol) was added to the reaction mixture and stirred for one more hour at RT. Solvent was evaporated and the crude residue was column purified (silica gel, 80% EtOAc/n-hexane) to afford Diisopropyl (R)-N-[2-(benzyloxycarbonylamino)-3-(4-phenoxyben-zenesulfonamido)propyl]carbamoylphosphonate as colorless solid in 82% (0.165 g, 0.31 mmol) yield.

Mp: 105-108° C.; NMR (CDCl$_3$) $^{31}$P: δ −4.00 ppm. $^1$H: δ 1.19-1.29 (m, 12H), 2.87-2.97 (m, 2H), 3.34-3.55 (m, 2H), 3.63-3.77 (m, 1H), 4.60-4.77 (m, 2H), 4.99 (s, 2H), 5.75 (d, 1H, J=7.2 Hz), 5.85 (t, 1H, J=6.0 Hz), 6.89-7.03 (m, 4H), 7.12-7.20 (m, 2H), 7.21-7.29 (m, 4H), 7.30-7.38 (m, 2H), 7.63-7.75 (m, 3H); MS-ES (m/z) 648 (M$^{+1}$).

e. (R)-N-[2-Amino-3-(4-phenoxybenzenesulfonamido)propyl]carbamoylphosphonic acid, Scheme 9E To a stirred solution of (R)-benzyl 1-(diisopropylphosphonoformamido)-3-(4-phenoxyphenylsulfonamido)prop-2-yl-carbamate (0.13 g, 0.2 mmol) in CHCl$_3$ (2 mL), was added dropwise TMSBr (0.26 mL, 2.0 mmol). The reaction mixture was stirred for 12 h at 50° C. Then two portions of 5 equivalents of TMSBr were added to the reaction mixture in an interval of 24 h. After completion of the reaction, solvent was evaporated. Methanol was added to the reaction mixture and stirred at RT for 1 h. Solvents were evaporated and the required (R)-N-[2-amino-3-(4-phenoxyphenylsulfonamido)propyl]carbamoylphosphonic acid was solidified as white solid in 64% (0.055 g) yield using EtOH.

Mp: 220-235° C.; NMR (D$_2$O+NaHCO$_3$) $^{31}$P: δ −1.17 ppm. $^1$H: δ 2.56-2.78 (m, 2H), 2.88-3.12 (m, 2H), 3.32-3.46 (m, 1H), 6.80-6.90 (m, 4H), 6.96-7.05 (m, 1H), 7.13-7.24 (m, 2H), 7.52 (dd, 2H, J=9.0, 2.4 Hz).

Enantiomeric Purity of the Optically Active Products

The enantiomeric purity of the two enantiomers of Compound 8, namely Compounds 8R and 8S, could not be ascertained by the use of polarimetry, because of the unusually small specific rotation values of the compounds. Consequently, two alternative methods were employed.

1) The Circular Dichroism (CD) of the two final enantiomeric products Compound 8R and Compound 8S exhibited (not shown) two mirror-image curves indicating for the S enantiomer and the R enantiomer.

2) The use of a Europium chiral shift reagent for the comparative examination of the $^1$H NMR spectra of the racemate and the two enantiomers provided further support for the eantiomeric purity of the compounds. In the absence of any shift reagent the two ring hydrogens ortho to the SO$_2$ group appeared as doublets at the lowest field in the spectra of each of the enantiomers and of the racemic mixture. Addition of 20 mg of Eu(hfc)$_3$ chiral shift reagent to the racemic mixture caused the doublet to split into two doublets and to move to lower field. In contrast, addition of portions of 20 mg of Eu(hfc)$_3$ to each of the enantiomers caused no change in the shapes of signals, only the doublets were shifted to lower field chemical shifts, which were different for each enantiomer. Addition of further amounts of the shift reagent caused no further changes in the signal shapes only moved the signals further downfield. These results indicate that the two optically active compounds were not contaminated by the opposite enantiomer in a concentration detectable by $^1$H NMR spectroscopy.

Biological Results

Compound 1 (JS-268) was found to be an active inhibitor for at least 3 hours in as demonstrated in FIG. 1, showing the time dependent inhibition over a period of 3 hours. The compound demonstrated specificity towards MMP-2 with reduced or no activity against MMP-9, MMP-8 and MMP-3. A moderate activity against TACE was also demonstrated (Tables 2 and 3).

In an in vitro model of tumor invasion of Compound 1 showed a substantial inhibitory profile (70% inhibition, Table 3). The compound was also evaluated in an in vivo experimental model of metastasis using B16F10 tumor cells in C57B1 mice. The compound showed significant inhibition in metastasis formation (>80% inhibition) as evaluated by the number of metastatic foci in the lung of the mice. The assay was carried out in a Boyden chamber with a reconstituted basement membrane (Matrigal).

A structure-activity relationship study (SAR) in which the carbon chain of the linker moiety having two CH$_2$ groups (Compound 1) was extended to five and six CH$_2$ groups (Compound 4 and Compound 5) was also conducted. As demonstrated in FIGS. 2 and 3, Compounds 4 and 5 exhibited improved inhibition, suggesting that generally chain elongation has an effect on the inhibitory activity of the compounds. As shown, chain elongation improved the activity of the inhibitor towards MMP-2 from 15 μM to 5 μM without compromising specificity. All compounds were active for at least 3 hours (the reactions have not been monitored longer than that, but the direction of the curves do not indicate a convergence).

In comparison to the control cis-ACCP (Tables 2 and 3), the structural modification demonstrated significantly altered inhibition, e.g., of cellular invasion (Table 3). However, the reduction in activity observed in the case of the inhibitors having shorter linker chains, in comparison to the control, arrested and in the inhibitors of the invention having extended linker chains, the activity was improved. It should be stated, once again, that a main characteristic of the compounds of the invention is their ability to inhibit MMP activity for longer periods of time in comparison to other carbamoylphosphonate MMP inhibitors previously developed.

It is important to note the effect of basic amine groups in the linker moieties. Two such compounds are shown in Tables 2 and 3. Compound 10 includes a secondary amine group in the linker moiety between to two carbon chains. This compound may be considered an isostere of Compound 4 having similarly a five-atom linker moiety. Comparison of the inhibition profiles of these two isosteres shows that the presence of the NH group reduced the inhibitory potency. In contrast, addition of a primary —NH$_2$ group to the three-carbon linker moiety to Compound 3 (JS-325) gives Compound 8 (JS-489) and enantiomers thereof. Comparison of these two compounds shows that the addition of the —NH$_2$ group endowed the resulting compound with considerable broad-spectrum potency. The time-dependent inhibition curves of Compound 8 (JS-489) displayed in FIGS. 4A-4E confirm the high affinity and the long term binding of these compounds to the five enzymes examined.

Figure 5:
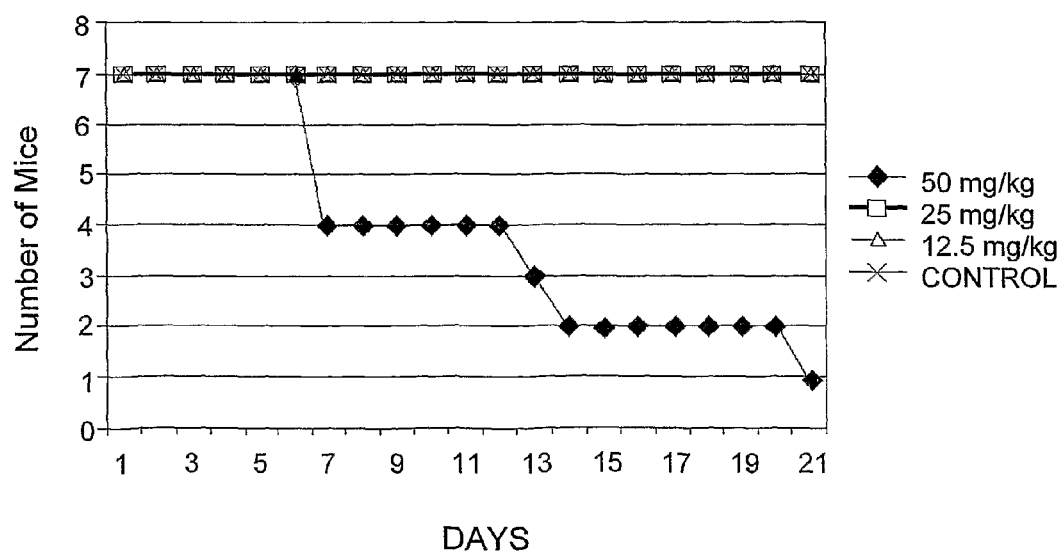
FIG. 5 illustrates the toxicity of Compound 5 as function of dose.

Compound 4 (JS-389) and Compound 5 (JS-403) have also been tested in vivo (Table 4). The initial dose was set to 50 mg/kg as in the previous studies. At this dose, Compound 4 exhibited significant inhibitory activity of metastasis formation (>80% inhibition), while Compound 5 was toxic at the same dose (FIG. 5). An additional study was conducted using the latter in two lower doses (25 and 12.5 mg/kg). At these doses, a dose dependent inhibition in metastasis formation was observed without any toxic effects.

Comparison of the in vivo results obtained at the lower doses for Compound 5 with those obtained for Compound 4 show that Compound 5 was more active at the 25 mg/kg dose in comparison to Compound 4 at the 50 mg/kg dose (Table 4).

TABLE 4

In vivo study into the effect of selected inhibitors of the invention on metastasis formation in mice.

| | | Dose mg/kg % reduction in lung metastases relative to control | | | |
|---|---|---|---|---|---|
| Inhibitors | Administration Mode | 12.5 mg/kg | 25 mg/kg | 50 mg/kg | 150 mg/kg |
| Compound 4 | Intraperitoneal | 57 % | 76 % | 90 % | N/A |
| Compound 4 | Per-oral | N/D | N/D | 80 % | 86 % |
| Compound 5 | Intraperitoneal | 82 % | 90 % | Toxic | N/A |
| Compound 5 | Per-oral | N/D | N/D | 50 % | 86 % |

The mice were injected i.v. with B16F10 cells and treated daily for three weeks.

Cancer Models

The ability of the compounds of the invention to inhibit tumor dissemination was tested in vitro and in vivo. Similarly to previous studies that had used hydroxamate-based inhibitors in doses of 50 mg/kg, identical dosing was used in the in vivo trials.

Determination of MMP Inhibitory Potency

Recombinant enzymes, human MMP-1, MMP-2, MMP-3, MMP-8, MMP-9, MMP-12, MMP-13 and TACE (R&D Systems, Minneapolis) were incubated at four different concentrations with the relevant colorimetric or fluorescent peptide substrates (R&D Systems, Minneapolis) for 3 h. The tested compounds were added at four to six different concentrations and the inhibitory potencies expressed in a colorimetric change, was measured by an ELISA or fluorimeter.

Murine Melanoma Model

Experimental metastasis was studied in the murine melanoma model. In this model, B16F10 tumor cells (50 k) were injected into the tail vein of C57B1 6 week old female mice. After 21 days, the metastases formed on the lungs of the mice were counted after appropriate fixation. Three groups of 8 mice were used in this study. Two groups of 8 mice were treated with daily (except weekends) administration of 50 mg/kg of the relevant inhibitor of the invention. One group received the inhibitor intraperitoneally and the other group orally, dissolved in PBS. Mice were monitored for toxic symptoms at alternate days.

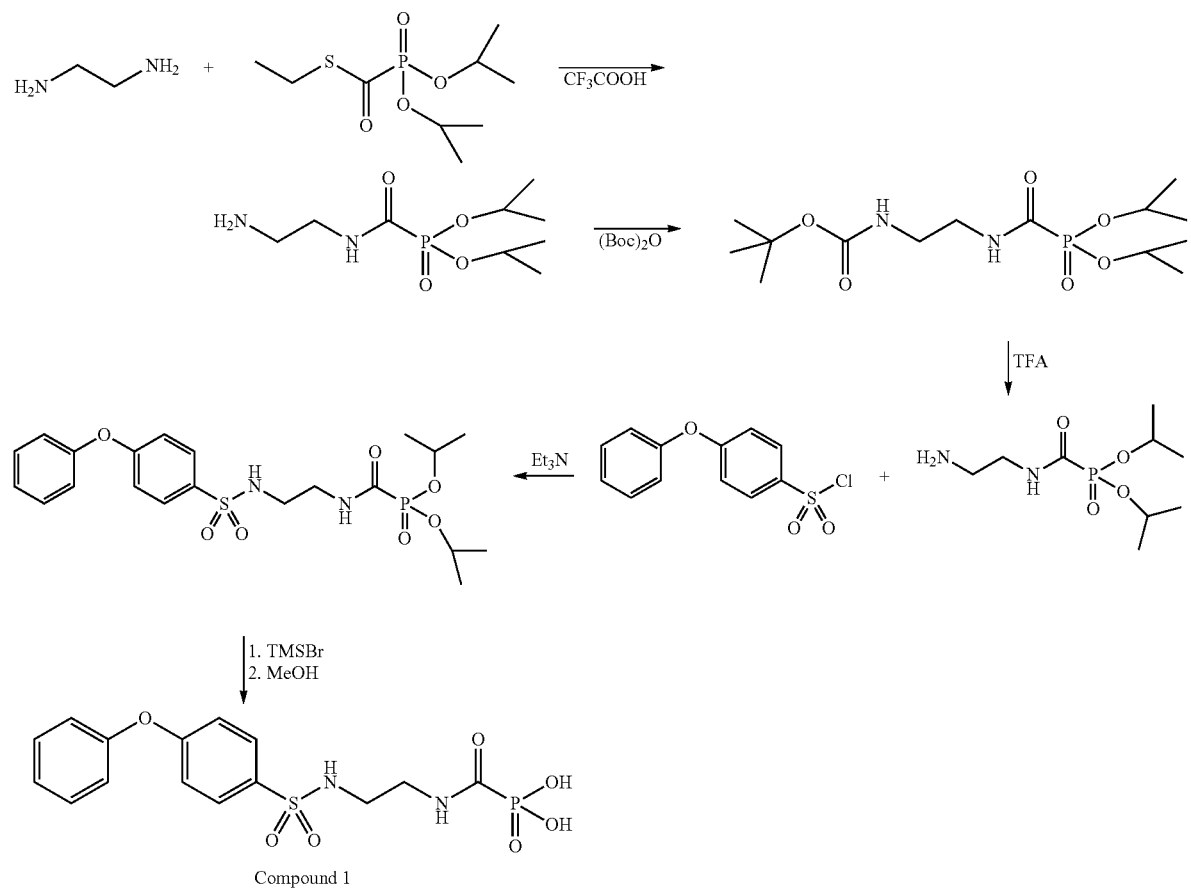

Scheme 1

Compound 1

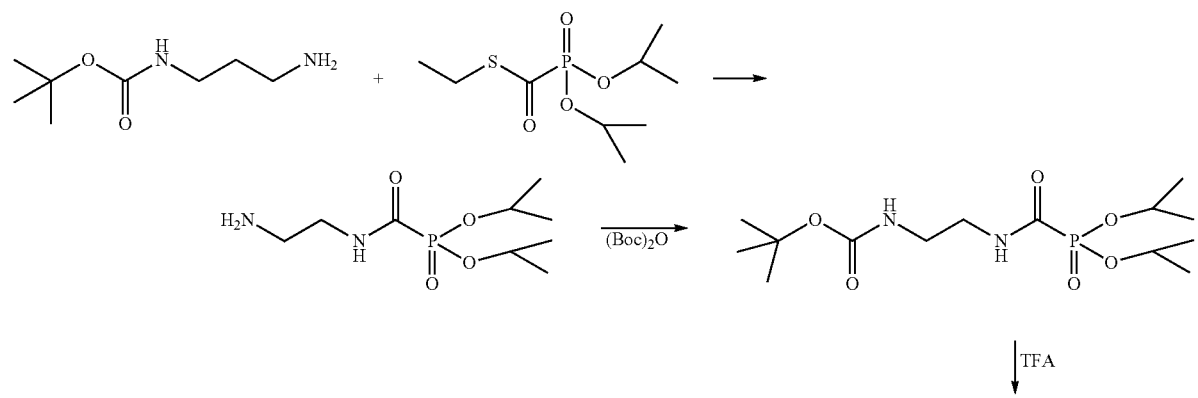

Scheme 2

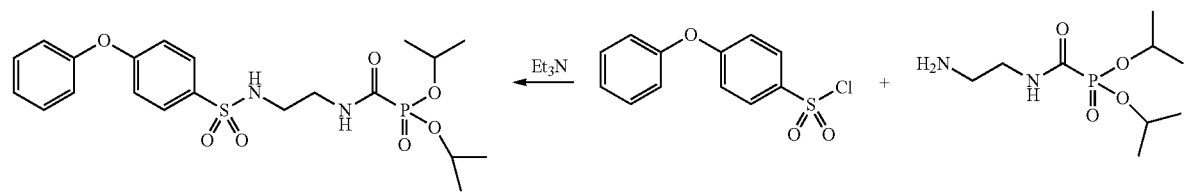
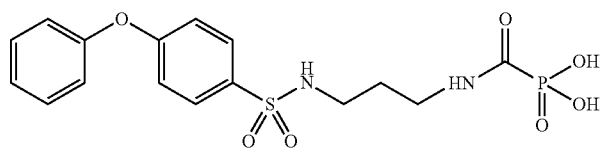
Compound 2
Scheme 3
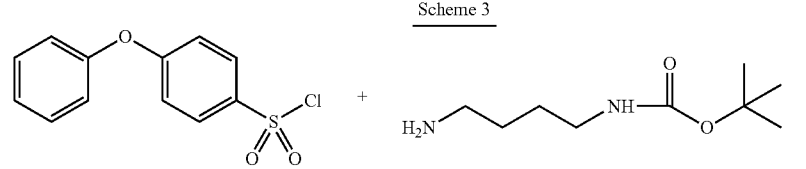
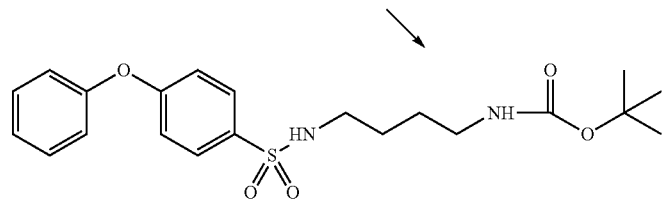
CF₃COOH
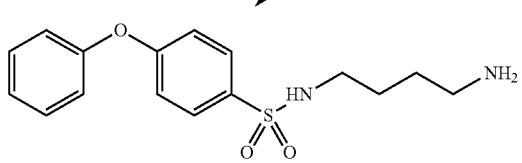
NPPF-E
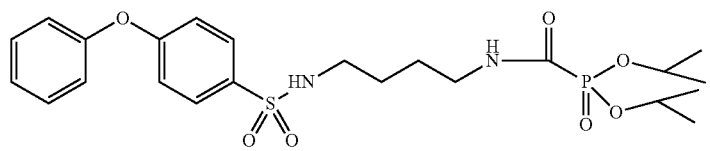
1. TMSBr
2. MeOH
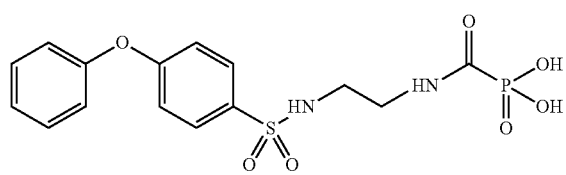
Compound 3

41                                                                42
-continued
Scheme 4
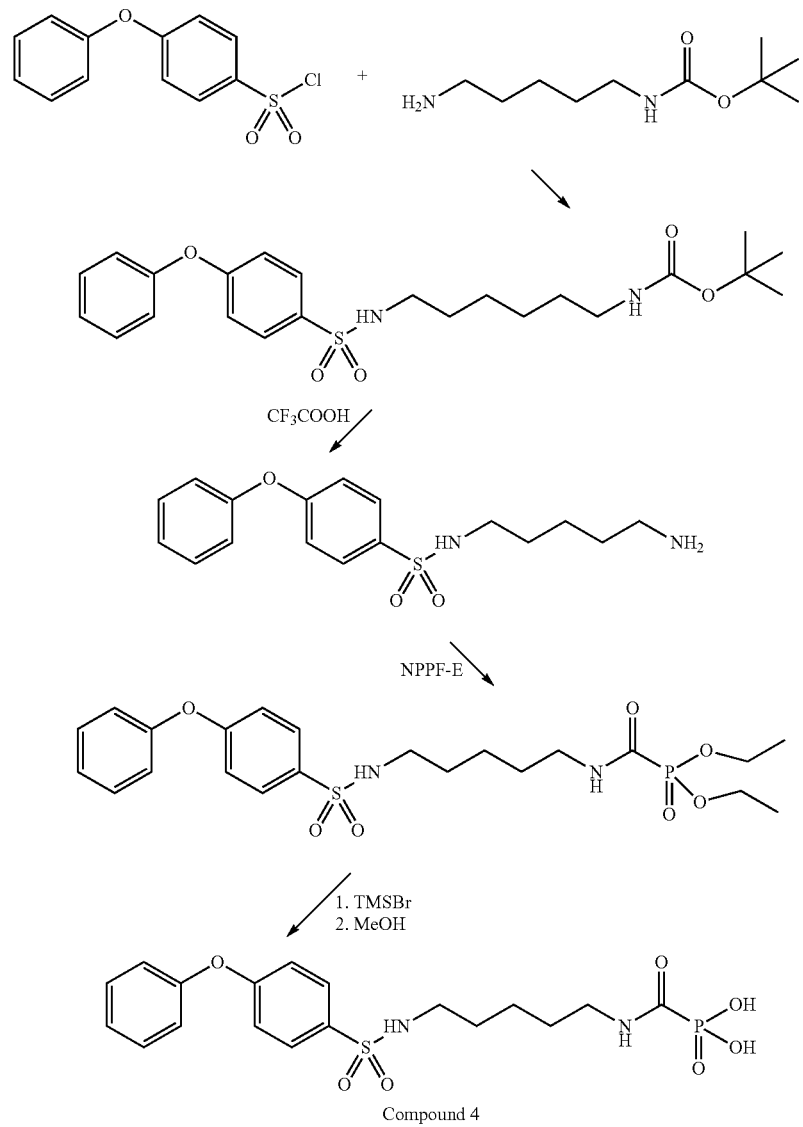
Compound 4
Scheme 5
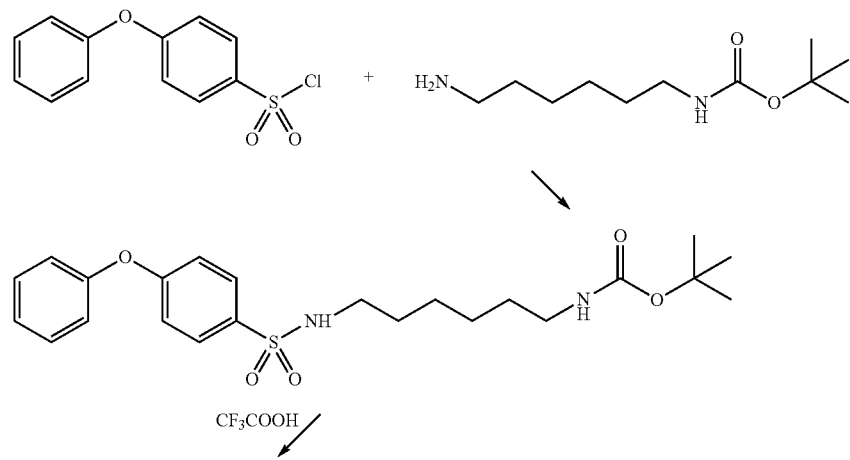

-continued
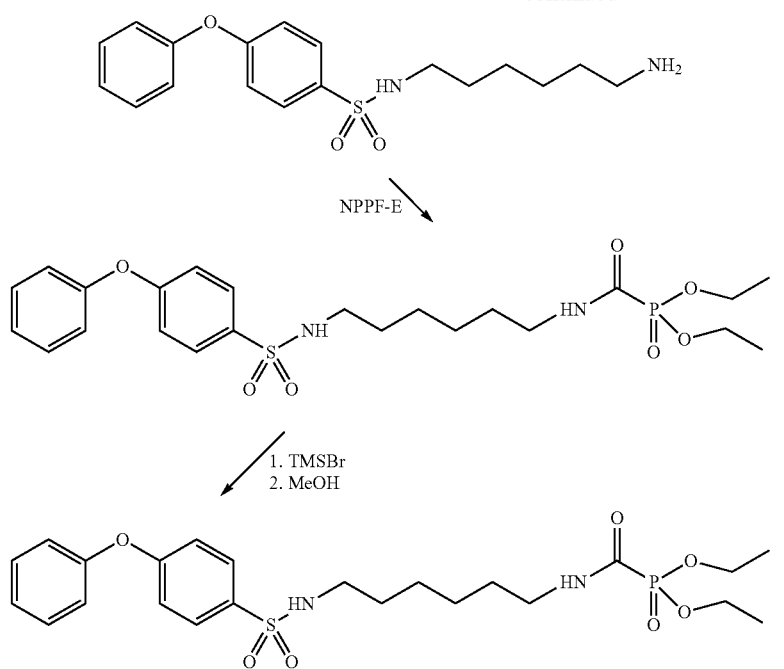
Compound 5
Scheme 6
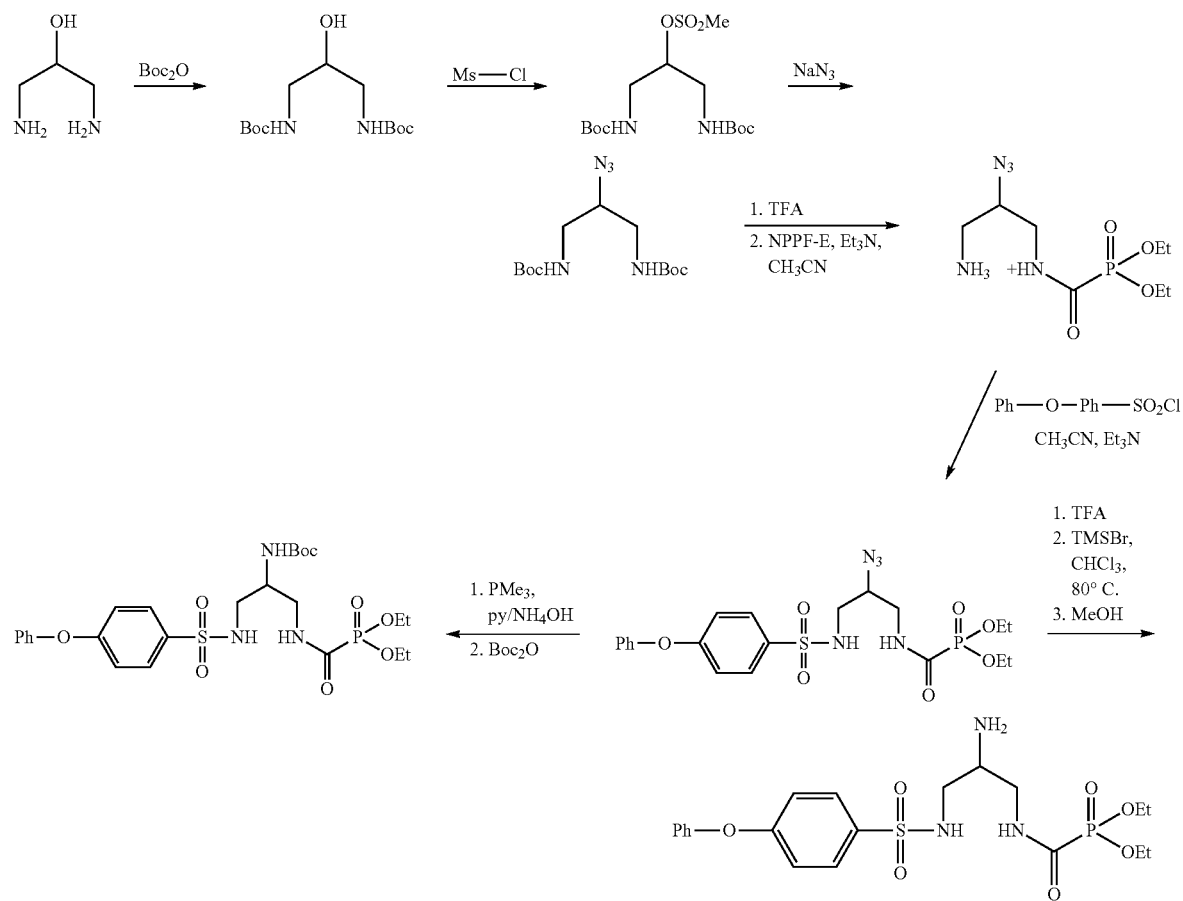

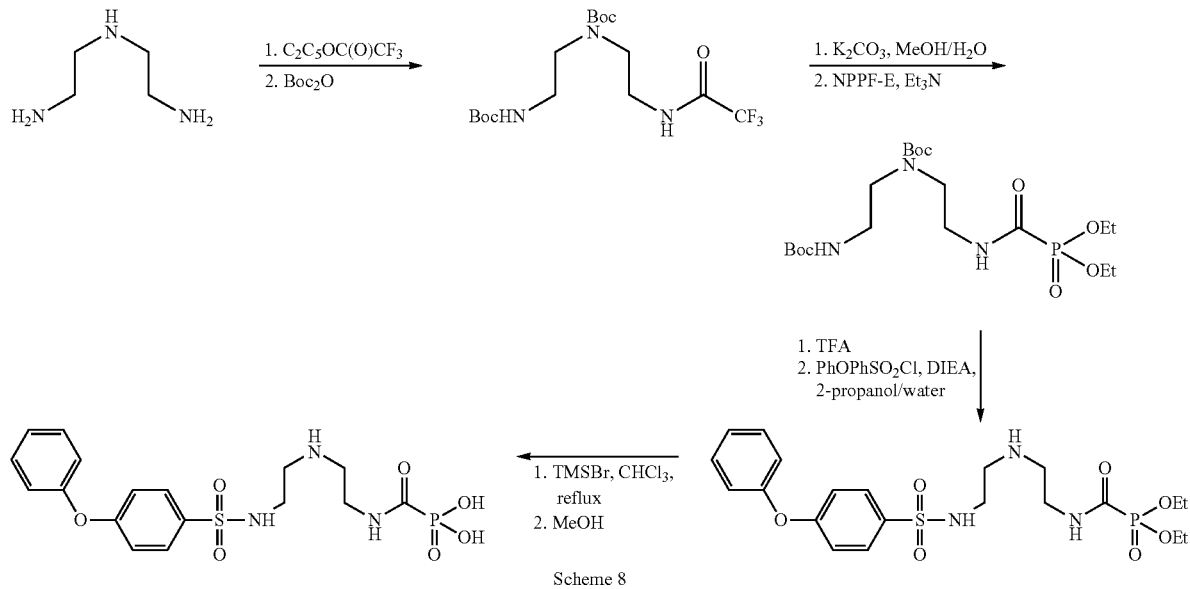
Scheme 8
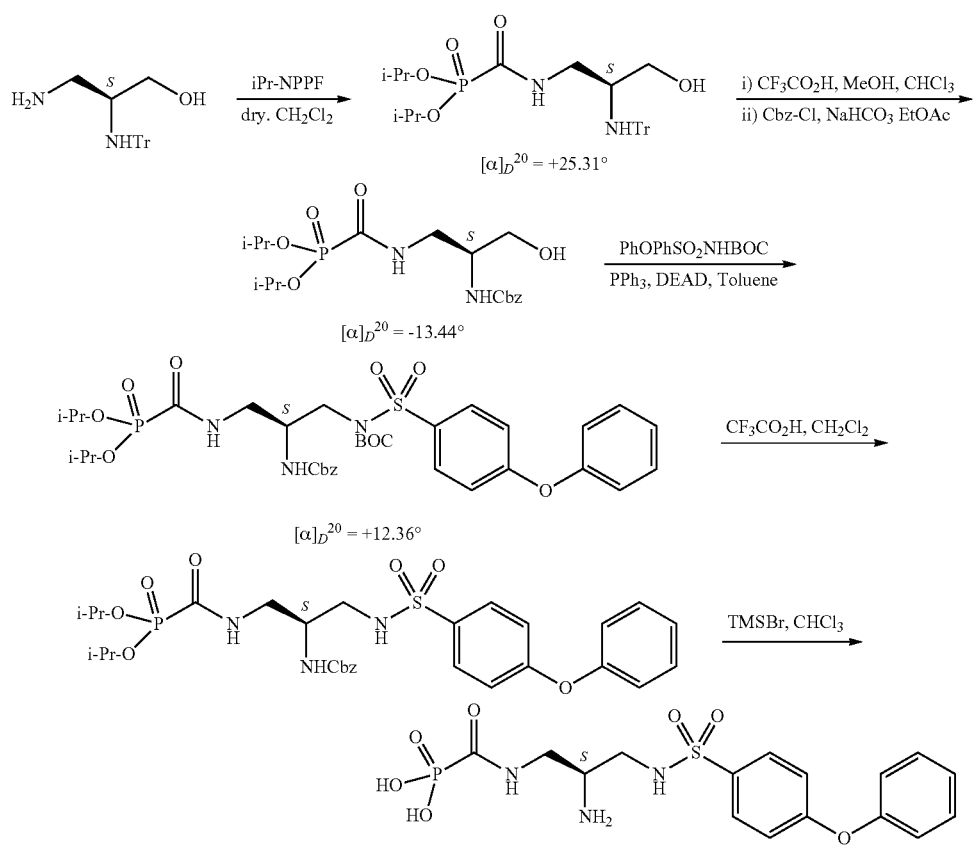
Scheme 8A
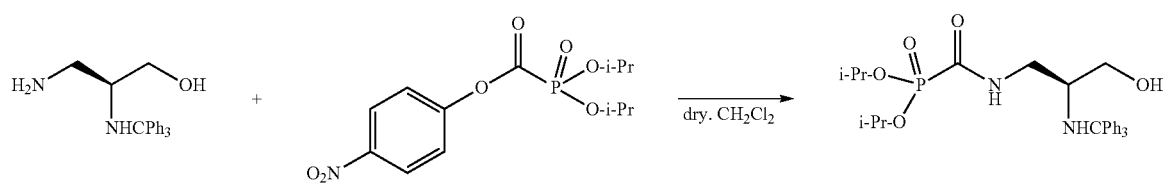

-continued
Scheme 8B
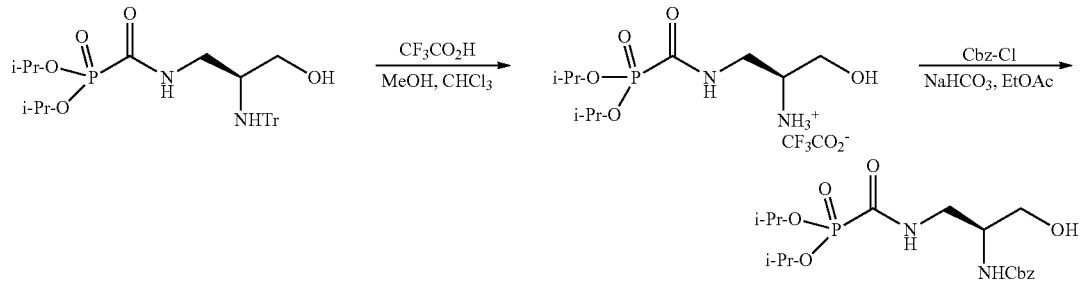
Scheme 8C
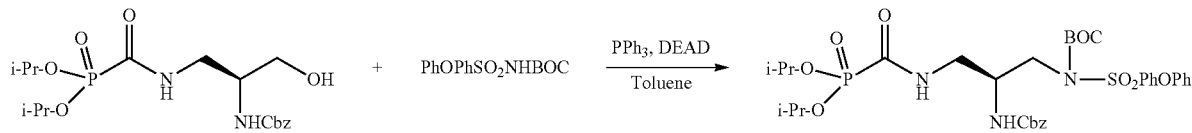
Scheme 8D
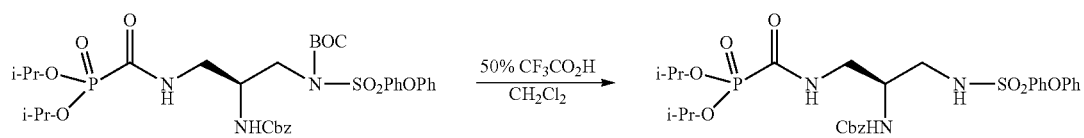
Scheme 8E
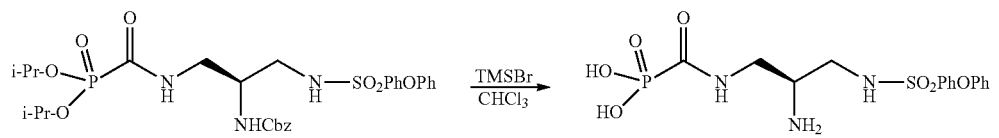
Scheme 9
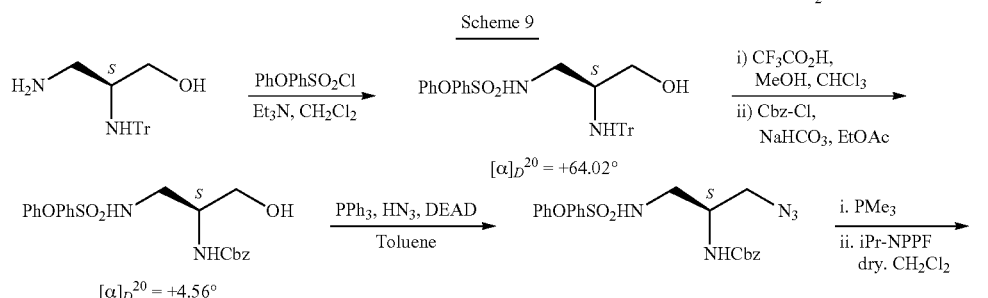
Scheme 9A
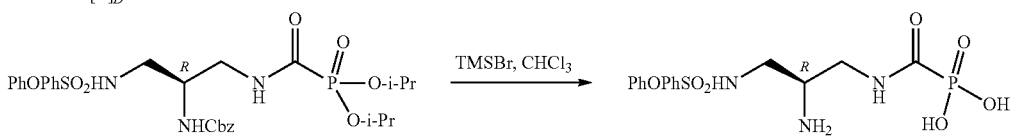
Scheme 9B
Scheme 9C
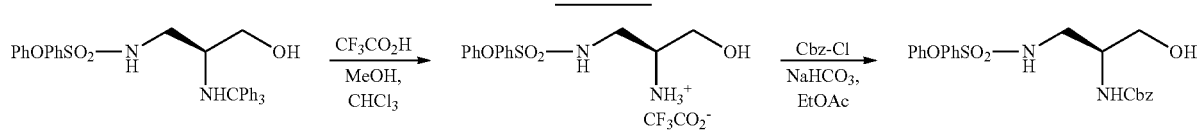
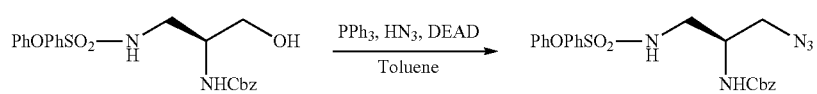

-continued

Scheme 9D

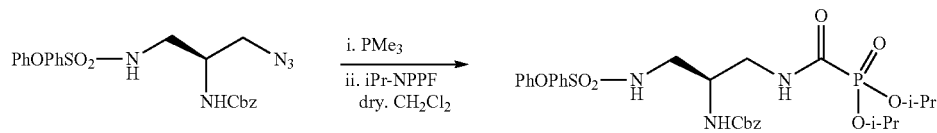

Scheme 9E

The invention claimed is:

1. A compound defined by formula (II):

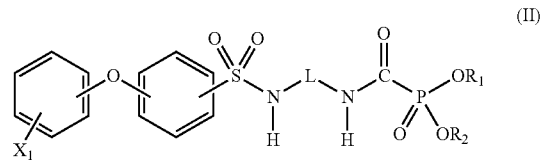

wherein
L is a $C_1$-$C_{10}$-alkylene, being optionally substituted with A;
$X_1$ is at least one substituent selected from —H; halo; —$C_1$-$C_6$-alkyl; —$C_2$-$C_6$-alkenyl; —$C_2$-$C_6$-alkynyl; —$C_3$-$C_6$-cycloalkyl; —$C_6$-$C_{10}$-aryl; —$CF_3$; —OH; —O—$C_1$-$C_6$-alkyl; —$NO_2$; —NHC(O)$R_3$; and —NR'R", each of said R' and R" independently of each other is selected from —H and —$C_1$-$C_6$-alkyl;
each of $R_1$ and $R_2$, independently of each other, is selected from —H, —$C_1$-$C_6$-alkyl, —$CR_4R_5$—O—(O)C—$C_1$-$C_6$-alkyl and a cation;
$R_3$ is selected from —$C_1$-$C_6$-alkyl; —$C_2$-$C_6$-alkenyl; —$C_2$-$C_6$-alkynyl; —$C_3$-$C_6$-carbocyclic rings; —O—$C_1$-$C_6$-alkyl; —$CF_3$; and —$C_6$-$C_{10}$-aryl;
each of $R_4$ and $R_5$, independently of each other, is selected from —H and $C_1$-$C_6$-alkylene; and
A is selected from —H; halo; $C_1$-$C_6$-alkyl; —$C_2$-$C_6$-alkenyl; —$C_2$-$C_6$-alkynyl; —$C_3$-$C_6$-cycloalkyl; —$CF_3$; —$C_6$-$C_{10}$-aryl; OH; —O—$C_1$-$C_6$-alkyl; —$NO_2$; —$N_3$; and —NR'R", wherein each of said R' and R" independently of each other is selected from —H, —$C_1$-$C_6$-alkyl and —C(O)O-t-Bu.

2. The compound according to 1, being a compound of formula (III):

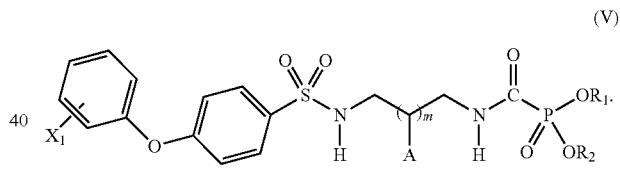

wherein
n is an integer from 2 to 10.

3. The compound according to claim 1, wherein the L is a $C_2$-$C_{10}$-alkylene substituted by at least one substituent A.

4. The compound according to claim 3, being a compound of formula (IV):

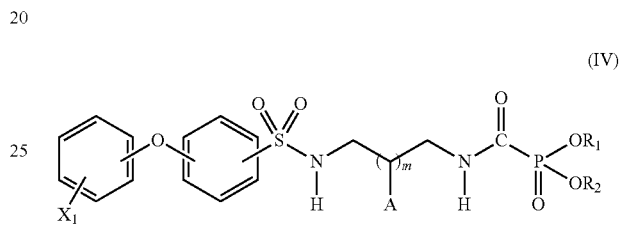

wherein
m is from 0 to 8.

5. The compound according to claim 4, being a compound of formula (V):

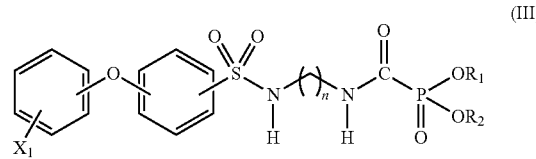

6. The compound according to claim 5, wherein each one of $X_1$, $R_1$ and $R_2$ is —H or $C_1$-$C_6$-alkyl, and A is selected from —H and —NR'R".

7. The compound according to claim 6, wherein each of A, $X_1$, $R_1$ and $R_2$ is —H.

8. The compound according to claim 5, wherein each of $X_1$, $R_1$ and $R_2$ is —H and A is not —H.

9. The compound according to claim 5, wherein m is 1 and A is —NHR".

10. The compound according to claim 9, wherein m is 1 and A is —$NH_2$.

11. The compound according to claim 5, wherein each of A and $X_1$ are —H and each of $R_1$ and $R_2$, independently of each other, is $C_1$-$C_6$-alkyl.

12. The compound according to claim 11, wherein each of $R_1$ and $R_2$, independently of each other is selected from $C_1$-$C_3$-alkyl.

13. The compound according to claim 12, wherein m is 0 or 1 and each of $R_1$ and $R_2$ is iso-propyl.

14. The compound according to claim 12, wherein m is 2, 3 or 4 and each of $R_1$ and $R_2$ is ethyl.

15. The compound according to claim 5, wherein $X_1$ is —H, each of $R_1$ and $R_2$ is $C_1$-$C_6$-alkyl or —$CR_4R_5$—O(O)C—$C_1$-$C_6$-alkyl and A is not —H.

16. The compound according to claim 15, wherein m is 1 and A is selected from —N$_3$ and —NRR", wherein R' is —H and R" is selected from —C$_1$-C$_6$-alkyl and —C(O)O-t-Bu.

17. A compound defined by formula (VI):

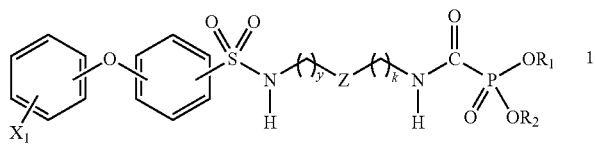

(VI)

wherein
- X$_1$ is at least one substituent selected from —H; halo; —C$_1$-C$_6$-alkyl; —C$_2$-C$_6$-alkenyl; —C$_2$-C$_6$-alkynyl; —C$_3$-C$_6$-cycloalkyl; —C$_6$-C$_{10}$-aryl; —CF$_3$; —OH; —O—C$_1$-C$_6$-alkyl; —NO$_2$; —NHC(O)R$_3$; and —NR'R", each of said R' and R" independently of each other is selected from —H and —C$_1$-C$_6$-alkyl;
- each of R$_1$ and R$_2$, independently of each other, is selected from —H, —C$_1$-C$_6$-alkyl, —CR$_4$R$_5$—O—(O)C—C$_1$-C$_6$-alkyl and a cation;
- Z is O or —NR$_6$;
- R$_6$ is selected from —H; —C$_2$-C$_6$-alkenyl; —C$_2$-C$_6$-alkynyl; —C$_3$-C$_6$-cycloalkyl; —CF$_3$; and —C$_6$-C$_{10}$-aryl; and
- each of k and y, independently of each other is an integer between 1 and 9.

18. The compound according to claim 17, wherein Z is oxygen.

19. The compound according to claim 17, wherein Z is —NR$_6$.

20. The compound according to claim 17, being a compound of formula (VII):

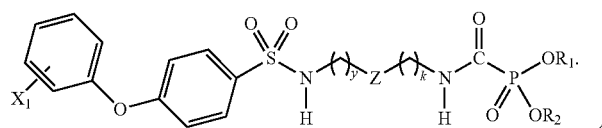

(VII)

21. The compound according to claim 20, wherein each of X$_1$, R$_1$ and R$_2$ is —H, Z is —NH, and each of k and y is 2.

22. A compound selected from the following Compounds:

Compound 1

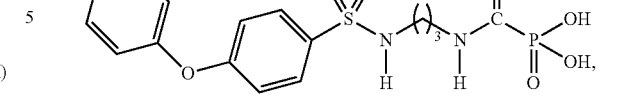

Compound 1A

Compound 2

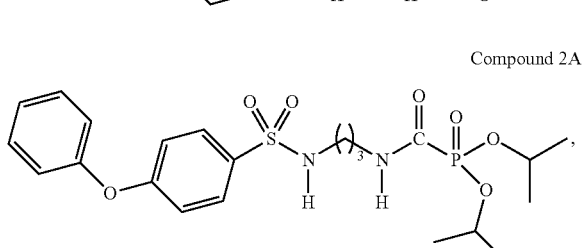

Compound 2A

Compound 3

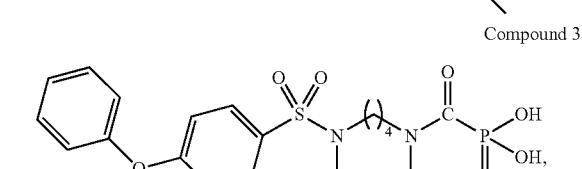

Compound 3A

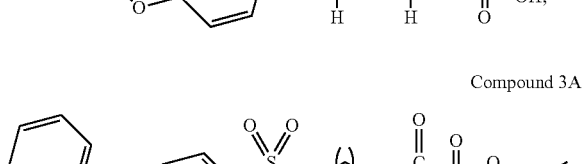

Compound 4

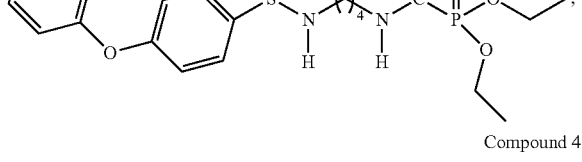

Compound 4A

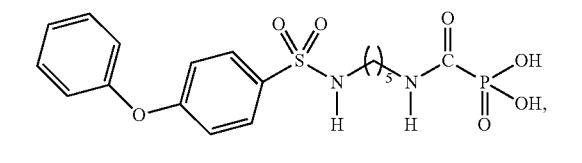

Compound 5

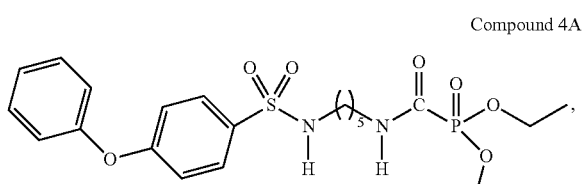

Compound 5A

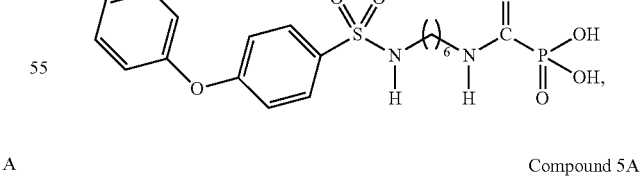

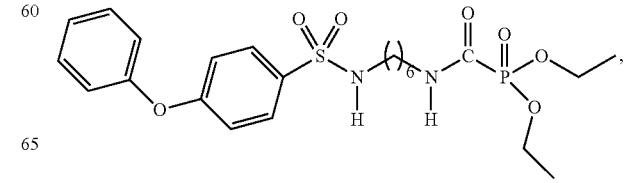

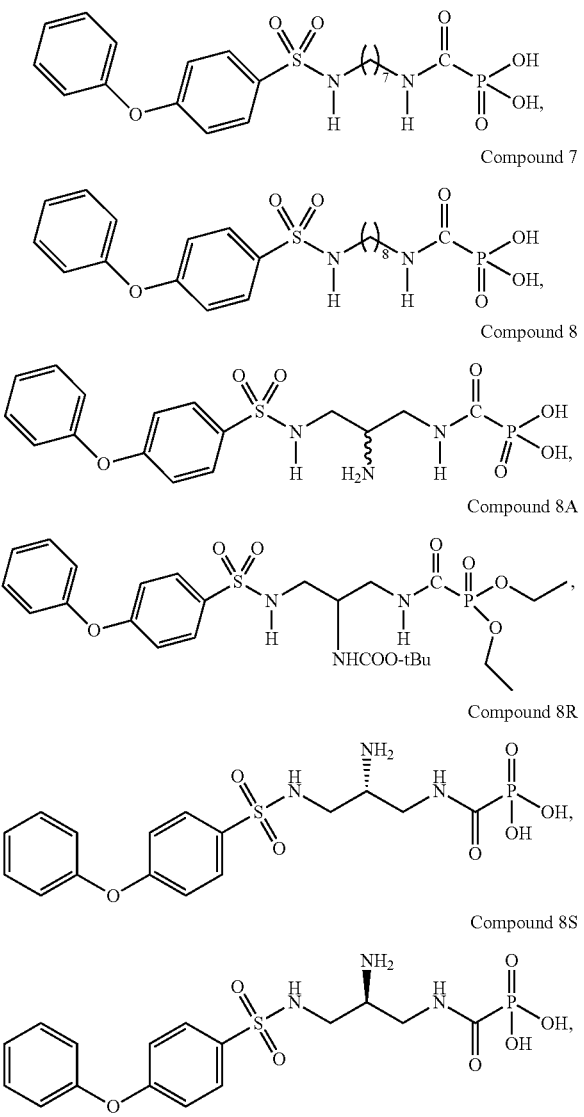
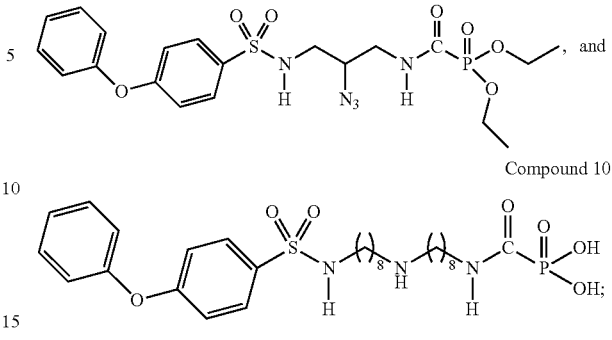

wherein said compound is in a form selected from salt, internal salt, hydrate, polymorph, racemic, stereoisomeric and diastereomeric mixtures.

23. A composition comprising at least one compound according to claim 1 and a carrier or an excipient.

24. A method of inhibiting metastasis of a melanoma in a subject which comprises administering an inhibitorily effective amount of a compound of claim 1 to the subject.

25. A method of inhibiting a matrix metalloproteinase-2 (MMP-2) which comprises exposing an MMP-2 to an inhibitorily effective amount of a compound of claim 1.

26. The method of claim 25, wherein said compound is administered to a subject and the exposure occurs in the body of the subject.

27. The method of claim 26, wherein the subject is suffering from an inflammatory disease or from a cancer.

28. A method of inhibiting metastasis of a melanoma in a subject which comprises administering an inhibitorily effective amount of a compound of claim 17 to the subject.

29. A method of inhibiting a matrix metalloproteinase-2 (MMP-2) which comprises exposing an MMP-2 to an inhibitorily effective amount of a compound of claim 17.

30. The method of claim 29, wherein said compound is administered to a subject and the exposure occurs in the body of the subject.

31. The method of claim 30, wherein the subject is suffering from an inflammatory disease or from a cancer.

32. A composition comprising at least one compound according to claim 17 and a carrier or an excipient.

\* \* \* \* \*

UNITED STATES PATENT AND TRADEMARK OFFICE
CERTIFICATE OF CORRECTION

PATENT NO. : 8,993,544 B2
APPLICATION NO. : 13/148421
DATED : March 31, 2015
INVENTOR(S) : Eli Breuer et al.

Page 1 of 1

It is certified that error appears in the above-identified patent and that said Letters Patent is hereby corrected as shown below:

In the claims
At Claim 13, col. 50, line 61, delete "m is 0or" and insert -- m is 0 or --.
At Claim 16, col. 51, line 2, delete "and -NRR", wherein" and insert -- and -NR'R", wherein --.
At Claim 17, col. 51, line 26, delete "-H; -$C_2$-$C_6$-alkenyl" and insert -- H; -$C_1$-$C_6$-alkyl; -$C_2$-$C_6$-alkenyl --.
At Claim 22, col. 54, lines 10-15, delete "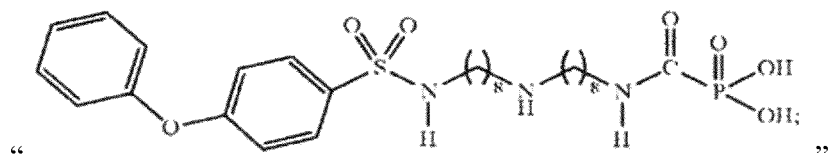"

and insert

-- 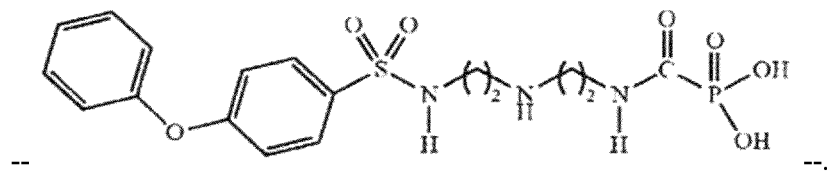 --.

Signed and Sealed this
Seventeenth Day of May, 2016

Michelle K. Lee
*Director of the United States Patent and Trademark Office*